(12) United States Patent
Jin et al.

(10) Patent No.: US 10,272,039 B2
(45) Date of Patent: Apr. 30, 2019

(54) TOPICAL SODIUM NITRITE FORMULATION

(71) Applicant: The United States of America, as represented by the Secretary, Department of Health and Human Services, Washington, DC (US)

(72) Inventors: Haksong Jin, McLean, VA (US); George Grimes, Rockville, MD (US); Deborah Sperling, Woodbine, MD (US); Gopal Potti, Gaithersburg, MD (US); Caterina P. Minniti, Chevy Chase, MD (US); Gregory J. Kato, Woodbine, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/525,557

(22) PCT Filed: Nov. 10, 2015

(86) PCT No.: PCT/US2015/060015
§ 371 (c)(1),
(2) Date: May 9, 2017

(87) PCT Pub. No.: WO2016/077386
PCT Pub. Date: May 19, 2016

(65) Prior Publication Data
US 2017/0333345 A1 Nov. 23, 2017

Related U.S. Application Data

(60) Provisional application No. 62/077,622, filed on Nov. 10, 2014.

(51) Int. Cl.
*A61K 33/00* (2006.01)
*A61K 9/06* (2006.01)
*A61K 9/08* (2006.01)
*A61K 9/00* (2006.01)
*A61K 47/06* (2006.01)
*A61K 45/06* (2006.01)

(52) U.S. Cl.
CPC .............. *A61K 9/06* (2013.01); *A61K 9/0014* (2013.01); *A61K 33/00* (2013.01); *A61K 45/06* (2013.01); *A61K 47/06* (2013.01)

(58) Field of Classification Search
CPC ... A61K 9/00; A61K 9/06; A61K 9/08; A61K 33/00
See application file for complete search history.

(56) References Cited

U.S. PATENT DOCUMENTS 6,103,275 A * 8/2000 Seitz .................... A61K 9/0014
424/718
2006/0186005 A1* 8/2006 Ebnesajjad ........... B65B 25/008
206/363

FOREIGN PATENT DOCUMENTS

WO    WO 01/89572    11/2001

OTHER PUBLICATIONS

Lu et al., "A Retrospective Review of Acupuncture Use for the Treatment of Pain in Sickle Cell Disease Patients: Descriptive Analysis from a Single Institution," *Clin. J. Pain*, vol. 30:825-830, 2014.
Minniti et al, "Topical Sodium Nitrite is Effective in Reducing Leg Ulcer-Associated Pain in Patients with Sickle Cell Disease," *Blood*, vol. 122:2236, 2013.
Minniti et al, "Topical Sodium Nitrite is Effective in Reducing Leg Ulcer-Associated Pain in Patients with Sickle Cell Disease," poster presentation at the American Society for Hematology annual meeting Dec. 2, 2013.
Minniti et al., "Topical Sodium Nitrite for Chronic Leg Ulcers in Patients with Sickle Cell Anaemia: A Phase 1 Dose-Finding Safety and Tolerability Trial," *Lancet Haematol.*, vol. 1:e95-103, 2014.
Minniti et al., "A Phase 1 Dose-Escalation Trial of Topical Sodium Nitrate in Patients with Sickle Cell Anemia and Leg Ulcers: Evidence of in Human Effect on Blood Flow," *Haematologica*, vol. 99:230, 19th Congress of the European Hematology Association, 2014.
Minniti et al., "Vasculopathy, Inflammation, and Blood Flow in Leg Ulcers of Patients with Sickle Cell Anemia," *Am. J. Hematol.*, vol. 89:1-6, 2014.
Opländer et al., "Dermal application of nitric oxide releasing acidified nitrite-containing liniments significantly reduces blood pressure in humans," *Nitric Oxide* 26:132-140, 2012.
Opländer et al., "Characterization of novel nitrite-based nitric oxide generating delivery systems for topical dermal application," *Nitric Oxide* 28:24-32, 2013.
Ormerod et al., "Evaluation of the Efficacy, Safety, and Tolerability of 3 Dose Regimens of Topical Sodium Nitrite with Citric Acid in Patients with Anogenital Warts: A Randomized Clinical Trial," *JAMA Dermatol* vol. 151:854-861, 2015.

(Continued)

*Primary Examiner* — Samira J Jean-Louis
(74) *Attorney, Agent, or Firm* — Klarquist Sparkman, LLP

(57) ABSTRACT

A sodium nitrite formulation for topical administration is described. The formulation includes an aqueous solution of non-acidified sodium nitrite dispersed in a white petrolatum ointment. The concentration of sodium nitrite in the formulation is about 0.5% to about 3.0% by weight. To prepare the formulation, non-acidified sodium nitrite is completely dissolved in a small quantity of water, sterile filtered and dispersed in white petrolatum ointment.

9 Claims, 10 Drawing Sheets

(56) References Cited

OTHER PUBLICATIONS

Sreedevi et al., "Dermatologic Lesions in Diabetes Mellitus," *Diabetologia Croatica*, vol. 31-3:147-159, 2002.

"Topical Sodium Nitrite for Chronic Leg Ulcers in Adult Patients with Blood Disorders," ClinicalTrials.gov identifier: NCT01316796, Mar. 15, 2011.

Tucker et al., "Effect of Nitric-Oxide-Generating System on Microcirculatory Blood Flow in Skin of Patients with Severe Raynaud's Syndrome: A Randomised Trial," *Lancet*, vol. 354:1670-1675, 1999.

Vercellotti, "Ankle Ulcers in Sickle Cell Disease: A Topical Solution to a Vexing Problem?" *The Hematologist*, http://www.hematology.org/Thehematologist/Clinical-Trials/2611.aspx, published online Mar. 1, 2014.

Weller et al., "The Effects of Topical Treatment with Acidified Nitrite on Wound Healing in Normal and Diabetic Mice," *Nitric Oxide*, vol. 15:395-399, 2006.

\* cited by examiner

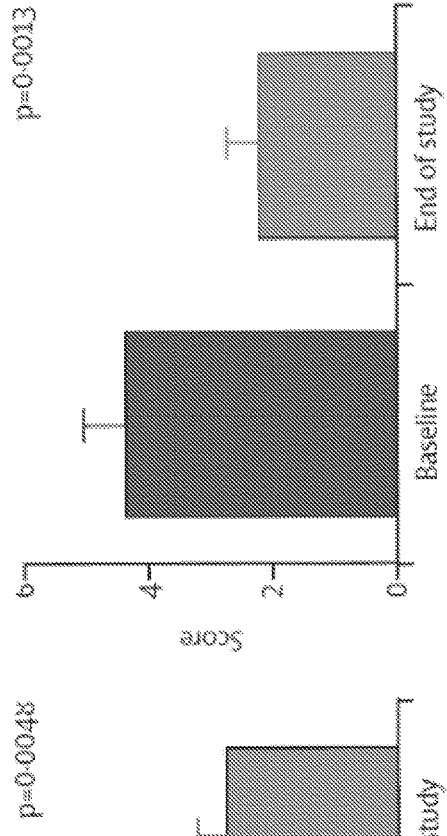
FIG. 3A Pain severity
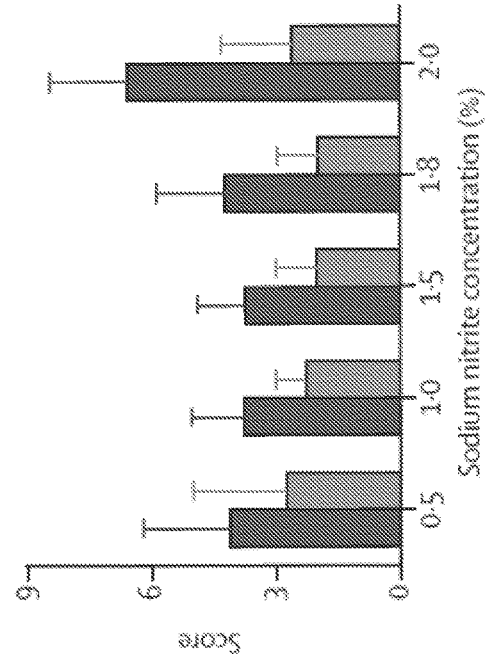
FIG. 3B Pain interference
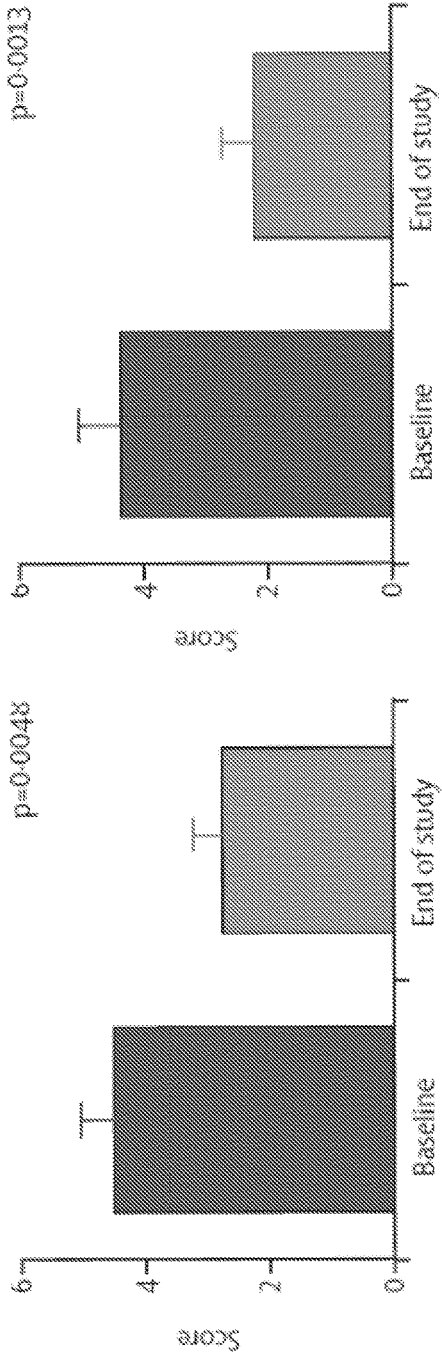
FIG. 3C Pain severity
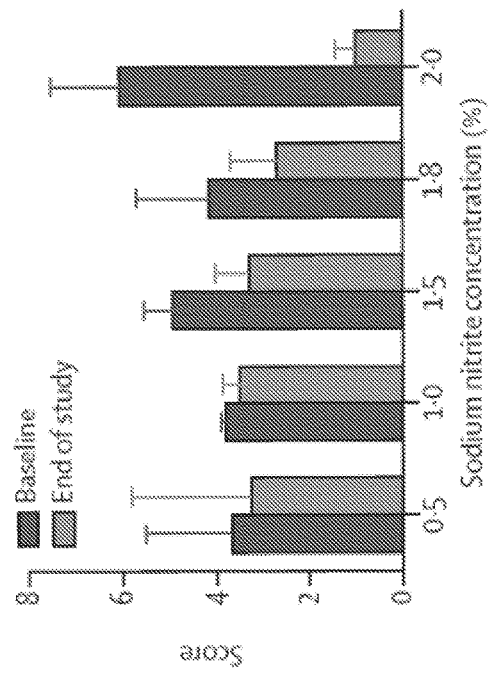
FIG. 3D Pain interference

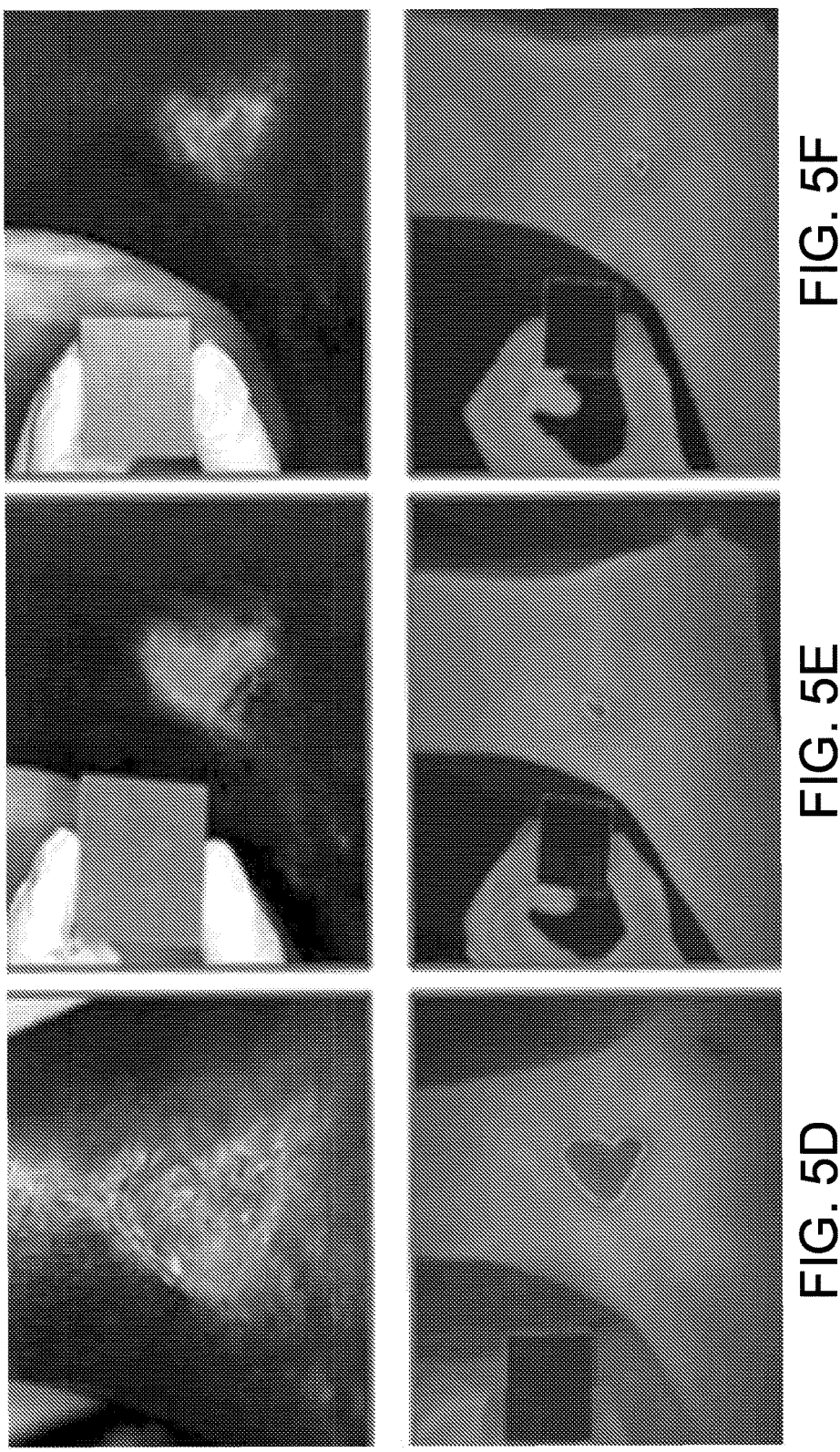

LCSI Baseline

LCSI after Sodium Nitrite

IR after Sodium Nitrite

IR Baseline

TOPICAL SODIUM NITRITE FORMULATION

CROSS-REFERENCE TO RELATED APPLICATIONS

This is the U.S. National Stage of International Application No. PCT/US2015/060015, filed Nov. 10, 2015, published in English under PCT Article 21(2), which claims the benefit of the earlier filing date of U.S. Provisional Patent Application No. 62/077,622, filed Nov. 10, 2014, which is incorporated herein by reference in its entirety.

BACKGROUND

Sickle cell disease is an autosomal recessive disorder and the most common genetic disease affecting African-Americans. Approximately 0.15% of African-Americans are homozygous for sickle cell disease, and 8% have sickle cell trait. Hemoglobin S polymerization leads to red cell rigidity, microvascular obstruction, inflammation, and end-organ ischemia-reperfusion injury and infarction. Up to 50% of sickle cell patients have endothelial dysfunction due to impaired bioavailability of endogenous nitric oxide (NO) due in large part to scavenging of nitric oxide by cell-free plasma hemoglobin. These data suggest that therapies directed at restoring NO bioavailability might prove beneficial. Between 8 and 20% of patients with sickle cell disease develop painful, disfiguring, and indolent leg ulcers, but higher rates of more than 50% have been reported (Serjeant, *Arch Intern Med* 133:690-694, 1974; Akinyanju and Akinsete, *Trop Geogr Med* 31:87-91, 1979). The ulcers usually appear between the ages of 10 and 50 years and have been reported to be more frequent in males than in females in some studies. The etiology of leg ulcers is unclear. Trauma, infection, severe anemia, and warmer temperature predispose to ulcer formation. Decreased blood flow after the ulcer has healed often results in recurrence. One study reported that 37% of sickle cell anemia (SCA) patients suffering from pulmonary hypertension also have leg ulcers (De Castro et al., *Am J Hematol* 83:19-25, 2008). Therefore, there has been an association between leg ulcers and pulmonary hypertension as complications more common in the hemolytic phenotype. Current treatment options for leg ulcerations, including antibiotics, compression bandages, dressing changes, Unna boot compression dressing, silver and zinc oxide gauze, and maggot therapy tend to rely on stimulation of granulation formation in the wound. Pathological changes in the microcirculation associated with ulceration are not addressed.

Nitric oxide mediates essential biological processes, including vasodilatation, antimicrobial activity and wound healing (Fang, *J Clin Invest* 99:2818-2825, 1997; Bulgrin et al., *Wounds* 7:48-57, 1995; Kirk et al., *Surgery* 114:155-159, 1993). NO is manufactured on epithelial surfaces, such as the mouth and stomach, and on the skin surface in humans by sequential reduction of nitrate and nitrite. This relies on the synthesis of nitrite by the bacterial reduction of inorganic nitrate present in saliva or sweat.

SUMMARY

A sodium nitrite formulation for topical administration is disclosed. The formulation includes an aqueous solution of non-acidified sodium nitrite dispersed in a white petrolatum ointment, such as AQUAPHOR™. The concentration of sodium nitrite in the formulation is about 0.5% to about 3.0% by weight, such as about 0.5, 1.0, 1.5, 1.8, 2.0, 2.5 or 3.0% by weight.

Also disclosed is a container comprising the sodium nitrite formulation disclosed herein. In some cases, the container is lined with a non-stick, non-reactive coating, such as a polytetrafluoroethylene (e.g. TEFLON™) coating.

Further disclosed is a method of preparing the sodium nitrite formulation disclosed herein. In some embodiments, the method includes dissolving sodium nitrite powder in water to produce an aqueous solution of sodium nitrite; filtering the aqueous solution of sodium nitrite through a 0.22 micron filter; and dispersing the filtered aqueous solution of nitrite into the white petrolatum ointment. In some examples, the aqueous solution of sodium nitrite is about 20% to about 40% sodium nitrite, such as about 30% sodium nitrite. In some examples, the volume of the aqueous solution dispersed into the white petrolatum ointment is about 4% to about 5% v/w.

The foregoing and other features and advantages will become more apparent from the following detailed description of several embodiments, which proceeds with reference to the accompanying figures.

BRIEF DESCRIPTION OF THE FIGURES

FIG. 1A quantifies wound size measured by digital planimetry. FIG. 1B quantifies wound sizes measured manually (longest length and widest width). FIG. 1C illustrates changes in wound size according to sodium nitrite concentration. Arrows in (A FIG. 1) and (FIG. 1B) represent first application of sodium nitrite cream. Plotted points or bars are mean values and error bars are standard error of the mean. *$p=0.0058$ compared with first application. †$p<0.0001$. ‡$p=0.0001$. § $p=0.0008$.

FIG. 2A charts changes in VAS pain scores for the ulcer treated with topical sodium nitrite at all doses, from screening to the end of the study. FIG. 2B charts changes in VAS score for additional ulcers not treated with topical sodium nitrite (n=9). FIG. 2C charts changes in VAS scores for the study ulcer treated with sodium nitrite cream at different concentrations. FIG. 2D charts the mean weekly use of opioid analgesics (total morphine equivalents) by all patients at the beginning of treatment compared with the end of treatment. Error bars are standard deviations. VAS=visual analogue scale.

FIG. 3A-3D is a series of graphs illustrating changes in the brief pain inventory scores during treatment of leg ulcers with topical sodium nitrite. Significant reductions were recorded in the pain severity subscore (FIG. 3A) and the pain interference subscore (FIG. 3B) averaged from all treated patients after eight treatments over 4 weeks (n=18, paired t test). FIGS. 3C and 3D chart changes in scores according to sodium nitrite concentration. Bars indicate mean values and error bars are standard error of the mean.

FIGS. 4C and 4D illustrate subgroup analysis results categorized according to the concentration of sodium nitrite cream.

FIG. 5A-5F is a series of photographs showing visible spectrum (FIG. 5A-5C) and infrared (FIG. 5D-5F) images of a leg ulcer in a representative sickle cell disease patient throughout the treatment period, as indicated.

FIG. 7A shows pharmacokinetics analysis of methemoglobin by dose level cohort. FIG. 7B shows pharmacokinetics of plasma nitrite concentrations during the entire trial. FIG. 7C shows whole blood nitrite concentrations in relation to hydroxycarbamide use. FIG. 7D shows observed dose response of whole blood nitrite to hydroxycarbamide dose during the first 24 hours after sodium nitrite application.

DETAILED DESCRIPTION

I. Terms

Figure 1A:
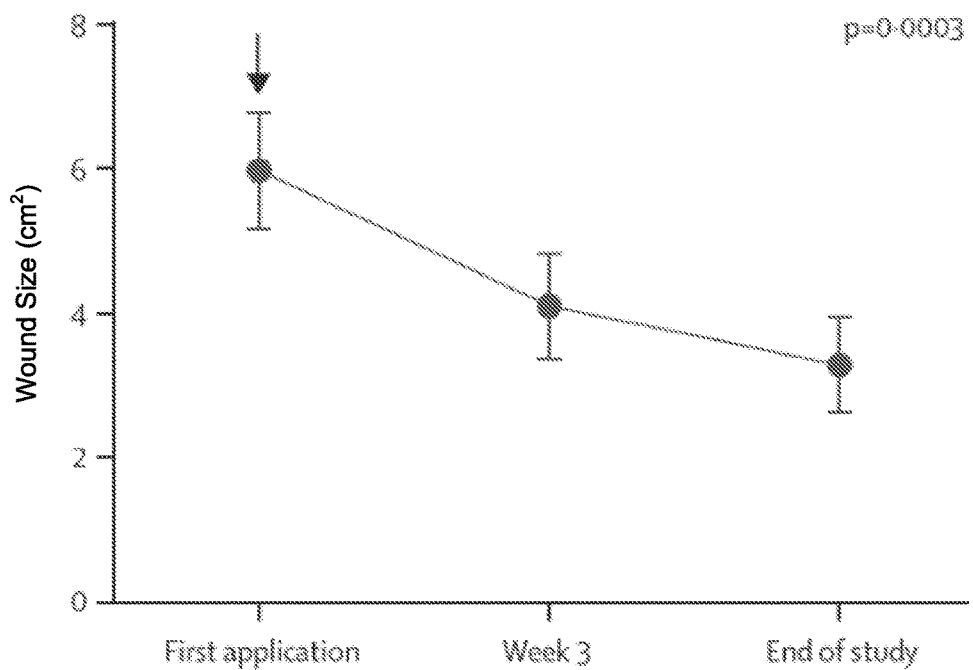
FIG. 1A-1C is a series of graphs illustrating changes in leg ulcer surface area before and after application of sodium nitrite cream.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent (e.g. non-acidified sodium nitrite), to a subject.

Antibiotic: A compound or substance that kills or substantially slows down the growth of bacteria, fungus or any other microbe. An "antibacterial" is a compound or substance that kills or substantially slows the growth of bacteria.

Antibacterial antibiotics are commonly classified based on their mechanism of action, chemical structure, or spectrum of activity. Most target bacterial functions or growth processes. Those that target the bacterial cell wall (for example, penicillins and cephalosporins) or the cell membrane (for example, polymixins), or interfere with essential bacterial enzymes (for example, quinolones and sulfonamides) are bactericidal. Those that target protein synthesis (for example, aminoglycosides, macrolides, and tetracyclines) are generally bacteriostatic. Further categorization is based on their target specificity.

"Narrow-spectrum" antibacterial antibiotics target specific types of bacteria, such as Gram-negative or Gram-positive bacteria. "Broad-spectrum antibiotics" affect a number of different types of bacteria. Antibacterial agents also include cyclic lipopeptides (such as daptomycin), glycylcyclines (such as tigecycline), and oxazolidinones (such as linezolid).

Topical antibiotics are antibiotics that are applied to a body surface, such as the skin or eye. Topical antibiotics are often formulated in an ointment or a cream, and contain active agents such as macrolide antibiotic (such as erythromycin), a sulfa antibiotic (such as sulfacetamide), a cyclic peptide (such as bacitracin a polymyxin) a psuedomonic acid (such as mupirocin), an ammyroglycoside (such as neomycin), or a quinolone (such as ciprofloxacin or ofloxacin), a nitroimidazole (such as metronidazloe), or a combination of drugs (such as bacitracine/polymyxin or neomycin/polymyxin B/bacitracin).

Co-administer/co-administration: To provide or give a subject a non-acidified sodium nitrite-containing composition disclosed herein with at least one other therapeutic agent within the same general time period. This term does not require administration at the same exact moment in time (although co-administration is inclusive of administering at the same exact moment in time). Thus, co-administration may be on the same day or on different days, or in the same week or in different weeks. The additional therapeutic agent may be included in the same composition as the sodium nitrite or it may be included in another composition, for instance as a separate topical application or systemically.

Cutaneous (dermal): Refers to the skin, which is the tissue forming the outer covering of the vertebrate body. The skin (which may also be referred to as the "integumentary system"), in combination with the mucous membranes (particularly the oral, nasal, oral and eyelid membranes) help protect the body from its external environment. The skin consists of two layers (the dermis and epidermis), the outermost of which may be covered in many animals (including humans) at least in part with hair. It is mainly protective and sensory in function, along with the mucous membranes of the eye, nose and mouth.

Emollient: Descriptive of a substance that softens or soothes the skin.

Epithelial Cell: A closely packed cell that forms an epithelium, such as in the skin. There are several types of epithelium, including simple squamous epithelium, simple cuboidal epithelium, simple columnar epithelium, pseudostratified columnar epithelium, stratified squamous (nonkeratinized) epithelium, stratified cuboidal epithelium, and transitional epithelium.

Epithelial surface(s): Tissue made up of epithelial cells that cover the surfaces of the body. Epithelial surfaces include external surfaces such as the skin and mucosa of the mouth and nose, as well as the linings of internal body surfaces. "External" epithelial surfaces are those exposed to the surfaces of the body (such as the skin, and the lining of the nose and mouth) and that are accessible to direct application of creams or ointments to the surface without the use of instrumentation (such as endoscopes or scalpels).

Ischemia: A vascular phenomenon in which a decrease in the blood supply to a bodily organ, tissue, or part is caused, for instance, by constriction or obstruction of one or more blood vessels. Ischemia sometimes results from vasoconstriction, thrombosis or embolism. Ischemia can lead to direct ischemic injury, tissue damage due to cell death caused by reduced oxygen supply.

Methemoglobin: The oxidized form of hemoglobin in which the iron in the heme component has been oxidized from the ferrous (+2) to the ferric (+3) state. This renders the hemoglobin molecule incapable of effectively transporting and releasing oxygen to the tissues. Normally, there is about 1% of total hemoglobin in the methemoglobin form.

Methemoglobinemia: A condition in which a substantial portion of the hemoglobin in the blood of a subject is in the form of methemoglobin, making it unable to carry oxygen effectively to the tissues. Methemoglobinemia can be an inherited disorder, but it also can be acquired through exposure to chemicals such as nitrates (nitrate-contaminated water), aniline dyes, and potassium chlorate. It is not the presence of methemoglobin but the amount that is important in the clinical setting. The following provides rough indications of symptoms associated with different levels of methemoglobin in the blood: <1.7%, normal; 10-20%, mild cyanosis (substantially asymptomatic, though it can result in "chocolate brown" blood); 30-40%, headache, fatigue, tachycardia, weakness, dizziness; >35%, symptoms of hypoxia, such as dyspnea and lethargy; 50-60%, acidosis, arrhythmias, coma, convulsions, bradycardia, severe hypoxia, seizures; >70% usually results in death.

Nitrite: The inorganic anion $^-NO_2$ or a salt of nitrous acid ($NO_2^-$). Nitrites are often highly soluble, and can be oxidized to form nitrates or reduced to form nitric oxide or ammonia. Nitrite may form salts with alkali metals, such as sodium ($NaNO_2$, also known as nitrous acid sodium salt), potassium and lithium, with alkali earth metals, such as calcium, magnesium and barium, with organic bases, such as amine bases, for example, dicyclohexylamine, pyridine, arginine, lysine and the like. Other nitrite salts may be formed from a variety of organic and inorganic bases. In particular embodiments, the nitrite is a salt of an anionic nitrite delivered with a cation, which cation is selected from sodium, potassium, and arginine. Many nitrite salts are commercially available, and/or readily produced using conventional and well-recognized techniques.

Non-acidified: Descriptive of a composition to which no acidifying agent(s) have been added, other than any acidification that may result from the presence of active ingredient(s). For instance, a non-acidified sodium nitrite composition (or formulation) is one that contains sodium nitrite, but to which no acid is added. This is in contrast, for instance, to previously known formulations that contain sodium nitrite and citric acid, e.g., in an ointment, which is considered an acidified or acidic formulation (though to produce nitrous acid that generates oxides of nitrogen including NO, $N_2O_3$ and the nitrosating agent $NO^+$).

Penetration enhancer: Descriptive of a compound that improves drug delivery into the skin.

Pharmaceutically acceptable salt: A biologically compatible salt of a compound that can be used as a drug, which salts are derived from a variety of organic and inorganic counter ions well known in the art.

Pharmaceutically (or Therapeutically) effective amount: An amount of a compound (e.g., non-acidified sodium nitrite) sufficient to treat a specified disorder or disease or one or more of its symptoms and/or to prevent the occurrence of the disease or disorder. "Treatment" includes arresting further advancement of a disease, as well as reversing the disorder, inducing regression of lesions, or in some examples curing the disorder.

Polytetrafluoroethylene (PTFE): A synthetic fluoropolymer of tetrafluoroethylene that has numerous applications. The best known brand name of PTFE-based formulas is TEFLON™.

Sodium nitrite: An inorganic compound having the chemical formula $NaNO_2$.

Subject: An animal (e.g., a mammal, such as a human). A subject to be treated according to the methods described herein may be one who has been diagnosed with a disease or disorder involving a skin lesion, such as a chronic or acute skin lesion, including but not limited to subject diagnosed with sickle cell anemia, diabetes, or decubitus wounds, or one at risk of developing such a skin lesion. Also contemplated are subjects with an acute skin lesion, such as resulting from a thermal, chemical, or radiation burn. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

Surfactant: A compound that lowers the surface tension of a liquid, the interfacial tension between two liquids, or that between a liquid and a solid. Surfactants may act as detergents, wetting agents, emulsifiers, foaming agents, and dispersants. Polysorbates are a class of emulsifiers. Polysorbates are oily liquids derived from PEG-ylated sorbitan (a derivative of sorbitol) esterified with fatty acids.

Polysorbate 20 (polyoxyethylene (20) sorbitan monolaurate; commercial brand names include TWEEN® 20) is a polysorbate surfactant whose stability and relative non-toxicity allows it to be used as a detergent and emulsifier in a number of pharmacological applications. It is a polyoxyethylene derivative of sorbitan monolaurate, and is distinguished from the other members in the polysorbate range by the length of the polyoxyethylene chain and the fatty acid ester moiety. Polysorbae 40 (Polyoxyethylene (20) sorbitan monopalmitate), Polysorbate 60 (Polyoxyethylene (20) sorbitan monostearate) and Polysorbate 80 (Polyoxyethylene (20) sorbitan monooleate) are additional example surfactants.

Therapeutically effective amount: A quantity of a specified agent sufficient to achieve a desired effect in a subject being treated with that agent. For example, a therapeutically amount may be an amount of non-acidified sodium nitrite that is sufficient to provide a bioactive amount in a subject's epidermis or dermis. Ideally, a therapeutically effective amount of an agent is an amount sufficient to treat the disease or condition without causing a substantial cytotoxic effect in the subject. The therapeutically effective amount of an agent will be dependent on the subject being treated, the severity of the affliction, and the manner of administration of the therapeutic composition.

Topical: Application of a drug-containing (pharmaceutical) formulation to the skin to directly treat cutaneous disorders or the cutaneous manifestations of a disease, with the intent of substantially directing the pharmacological effect of the drug to the surface of the skin or within the skin. Topical dosage forms are typically semi-solid systems, but can include a variety of other dosage forms such as foams, sprays, medicated powders, solutions and medicated adhesive systems. Topical delivery includes external topical agents that are spread, sprayed, or otherwise dispersed on cutaneous tissues to cover the affected area, or internal topical agents that are applied to the mucous membranes orally, vaginally, or on anorectal tissues for local activity. The topical drugs disclosed herein can be administered in any topical dosage form, for example as a solid (powder, aerosol or plaster); liquid (lotion, liniment, solution, emulsion, suspension, or aerosol) or semi-solid (ointment, cream, paste, gel, jelly or suppository).

In particular examples the composition is applied to the skin (or the eye) in an area where re-epithelialzation is desired. For example the pharmaceutical composition can be applied in a topical preparation to a wound, such as an epithelial wound or defect, for example a traumatic or surgical wound, such as a skin or corneal abrasion or surgical incision.

Topical base: The solid component of a topical formulation. A therapeutically effective amount of an active compound (e.g., sodium nitrite) is combined with a topical base to produce a topical formulation such as an ointment, a cream, or a lotion. The topical formulation also may include additional components such as excipients, including, without limitation, antioxidants, binders, emollients, penetration enhancers, surfactants, and the like.

Treatment: Therapeutic intervention that ameliorates a sign or symptom of a disease or pathological condition after it has begun to develop. As used herein, the term ameliorate (or palliate), with reference to a disease or pathological condition, refers to any observable beneficial effect of the treatment. The beneficial effect can be evidenced, for example, by a reduction in severity of some or all clinical symptoms of the disease or condition, a slower progression of the disease or condition, an improvement in the overall health or well-being of the subject, or by other parameters well known in the art that are specific to the particular disease or condition. The phrase "treating a disease" or "treating skin damage" refers to inhibiting the full development of a disease or a skin condition, for example, in a subject who is at risk for a disease such as a chronic skin lesion, particularly lesions associated with sickle cell anemia, diabetes, burns, or decubitus wounds (pressure ulcers, bedsores).

White petrolatum: A semi-solid mixture of hydrocarbons obtained from petroleum, often used as a topical ointment base, topical protectant or lubricant. AQUAPHOR™ (Beiersdorf Inc.) skin ointment is comprised of white petrolatum (41%).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

II. Overview of Several Embodiments

A first embodiment is a formulation for topical administration, comprising an aqueous solution of about 0.5% to about 3.0% by weight non-acidified sodium nitrite dispersed in a white petrolatum ointment. By way of example, the white petrolatum ointment may comprise AQUAPHOR™ (41% petrolatum) ointment. The concentration of sodium nitrite in various formulation embodiments is 0.5, 1.0, 1.5, 1.8, 2.0, 2.5 or 3.0% by weight.

Another embodiment is a container comprising the sodium nitrite formulation/composition as described herein, wherein the container is lined with a substantially non-stick, non-reactive coating. For instance, in some cases the coating comprises polytetrafluoroethylene.

Also provided are methods of preparing the formulations described herein, which method comprises dissolving sodium nitrite powder in water to produce an aqueous solution of sodium nitrite having a concentration of about 20% to about 40% sodium nitrite; filtering the aqueous solution of sodium nitrite through a 0.22 micron filter; and dispersing the filtered aqueous solution of nitrite into the white petrolatum ointment. By way of example, in some such methods the concentration of the aqueous solution of sodium nitrite is about 30% sodium nitrite. Optionally, the volume of the aqueous solution dispersed into the white petrolatum ointment is about 4% to about 5% v/w.

III. Nitric Oxide and Vascular Function

NO is a soluble gas with a half-life of seconds, continuously synthesized in endothelial cells from the amino acid L-arginine by the nitric oxide synthase enzyme. In their seminal experiment, Furchgott and Zawadzki (*Nature* 288: 373-376, 1980) found that strips of rabbit aorta with intact endothelium relaxed in response to acetylcholine but constricted in response to the same agonist when the endothelium had been rubbed off. The substance responsible for acetylcholine-stimulated relaxation was initially called endothelium-derived relaxant factor, but was subsequently found to be nitric oxide (NO). NO released from the endothelium as a gas or attached to transport molecules activates soluble guanylyl cyclase in smooth muscle after binding to its heme group, resulting in increased cyclic GMP. Cyclic GMP activates GMP-dependent kinases that decrease intracellular calcium concentration in smooth muscle, producing relaxation.

Indeed, recent reports suggest that dysfunctional vascular NO production, characterized by a paradoxical vasoconstrictor response to acetylcholine (an agonist that normally increases blood flow by stimulating endothelial NO production) predicts future cardiac ischemic events (Vrints et al., *Eur Heart J* 13:824-831, 1992). Thus a deficiency in endothelial production of NO is increasingly being recognized as a mechanism in vascular diseases.

Sickle cell ulcers have been recognized to be associated with other complications, such as priapism and pulmonary hypertension, constituting a sub-phenotype of SCA, in which intravascular hemolysis and endothelial lesions play a key role (Kato et al., *Blood* 107:2279-2285, 2006). Indeed, in SCA, high levels of endothelin-1 and impaired bioavailability of nitric oxide exists, and leads to vasoconstriction and vasculopathy (Hebbel and Vercellotti, *J Lab Clin Med* 129:288-293, 1997; Tharaux et al., *Clin Sci* 87:671-677, 1994; Reiter et al., *Nat Med* 8:1383-1389, 2002).

IV. Reduced Nitric Oxide Bioavailability in Sickle Cell Disease

Recent clinical data suggest that patients with sickle cell disease also suffer from impaired nitric oxide bioavailability (Gladwin et al., *Circulation* 107:2279-2285, 2006). These data suggest that dysfunctional vascular endothelium may contribute to the clinical events suffered by patients with sickle cell disease. Previous studies have shown that the cell-free plasma hemoglobin resulting from intravascular hemolysis rapidly consumes NO, dramatically limiting its bioavailability in patients with sickle cell disease (Reiter et al., *Nat Med* 8:1383-1389, 2002). Thus hemolysis produces a state of resistance to NO-dependent vasodilation. Consistent with this, in patients with the highest plasma hemoglobin levels the blood flow responses to the NO donor, sodium nitroprusside were abolished. During vaso-occlusive pain crisis and the acute chest syndrome, hemolysis intensifies with increases of plasma hemoglobin by four-fold suggesting that NO scavenging or inactivation may have played a major role in vascular instability during crisis (Naumann et al., *Am J Clin Pathol* 56:137-147, 1971; Ballas and Marcolina, *Transfusion* 46:105-110, 2006). Chronic hemolysis produces a clinical syndrome of endothelial dysfunction that ultimately results in pulmonary hypertension, cutaneous ulceration, renal failure and possibly stroke in children (Kato et al., *Blood Rev* 21:37-47, 2007; Rother et al., *JAMA* 293:1653-1662, 2005; Jison and Gladwin, *Am J Respir Crit Care Med* 168:3-4, 2003). Therapeutic modalities based on the oxidation and inactivation of the plasma cell-free hemoglobin could potentially restore regional NO-dependent blood flow and improve acute pain symptoms due to vaso-occlusion, ischemia and infarction in patients with sickle cell disease (Mack and Kato, *Int J Biochem Cell Biol* 38:1237-1243, 2006).

V. Topical Sodium Nitrite Therapy

It has been determined that the nitrite anion acts as a vasodilator in vivo by generating nitric oxide (NO) in tissues with lower oxygen tension and pH (Huang et al., *J Clin Invest* 115:2099-2107, 2005; see also WO 2005/004884 by Gladwin et al., which is incorporated herein by reference). The mechanism involves a novel physiological function of human hemoglobin as an oxygen- and pH-dependent nitrite reductase. Therefore, nitrite provides the ideal substrate for NO generation along the physiological oxygen gradient, potentially providing a novel mechanism for hypoxic vasodilation.

It is believed that therapeutic application of sodium nitrite will provide selective vasodilation to hypoxemic tissue and could be used to treat diseases associated with ischemic tissue, neonatal pulmonary hypertension, and hemolytic conditions such as sickle cell disease, where free hemoglobin released during hemolysis scavenges NO and disrupts NO-dependent vascular function. Available data indicates that sodium nitrite will not only inhibit the ability of free hemoglobin (by oxidizing it to methemoglobin) to scavenge NO, but will actually generate NO in tissue beds with low oxygen tension (Crawford et al., *Blood* 107:566-574, 2006).

Previous data indicate that nitrite also favorably alters mitochondrial respiration in a manner that closely mimics ischemic preconditioning (Shiva et al., *Circ Res* 100:654-661, 2007). This process of providing small ischemic exposures to tissue confers a marked degree of protection against infarction of the tissue upon more prolonged subsequent tissue ischemia. The effect of nitrite on mitochondrial respiration may provide the mechanism for a significant component of the anti-infarctive properties of nitrite (Shiva and Gladwin, *Crit Car Med* 33:1865-1867, 2005).

VI. Conditions to be Treated

Topical sodium nitrite cream has been exemplified herein in the treatment of sklin lesions or ulcers in sickle cell patients, including let ulcers.

It is believed that the formulations and methods provided herein will be effective in the treatment of additional types of dermatological lesions, for instance those associated with type 1 or type 2 diabetes mellitus (see, e.g., Sreedevi et al., *Diabetologica Croatica* 31-3, 147-159, 2002), decubitus wounds/ulcers (pressure ulcers, bedsores), burns, and other dermatological wounds.

More generally, the formulations described herein are expected to be useful for the treatment of any wounds or other skin breakages, where it would be beneficial to increase the flow of blood to the area; to provide non-acidified sodium nitrite as a localized, topical source of nitric oxide; to reduce pain or the perception of pain; and/or to reduce microbial growth.

Certain embodiments concern a method for treating dermatological ulcers, such as ulcers in sickle cell or diabetes patients, decubitus (pressure) ulcers, venous leg ulcers, burns, or other dermatological/cutaneous wounds. For example, the method may comprise topically administering to a subject a disclosed embodiment of the pharmaceutical formulation. For particular embodiments, the method comprises identifying a subject having cutaneous lesion(s). A disclosed embodiment, or embodiments, of the pharmaceutical formulation (that is, comprising non-acidified sodium nitrite) is applied topically to the subject's cutaneous lesions. The disclosed method contemplates using any one of the disclosed embodiments of the pharmaceutical formulation. In particular disclosed embodiments, the method may comprise using a pharmaceutical formulation comprising: at least 0.5% and up to 3% sodium nitrite suspended in a topical base.

The present disclosure provides embodiments of topical formulations including non-acidified sodium nitrite, salts, and solvates thereof, for use in treating diseases and/or disorders of the skin and/or mucous membranes, and in particular lesions caused or exacerbated by sickle cell anemia or diabetes, as well as decubitus wounds, burns, and other dermatological lesions. Non-acidified sodium nitrite may be administered alone or in combination with other agents.

As used herein, and as well understood in the art, "treatment" is an approach for obtaining beneficial or desired results, including clinical results. For the purposes of this disclosure, beneficial or desired results can include one or more, but are not limited to, alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease, state, and remission (whether partial or total), whether detectable or undetectable. Non-acidified sodium nitrite is potent and can be administered locally (for example topically or by injection to the skin or mucous membrane) at very low doses, thus minimizing systemic adverse effects. It is believed that this treatment also avoids the side-effects caused by more standard treatments, and is highly effective because of its direct application to affected areas.

Non-acidified sodium nitrite, or pharmaceutical compositions comprising it, will generally be used in an amount effective to achieve the intended result, for example in an amount effective to treat the subject's particular condition. The compound is administered to achieve a therapeutic benefit. By therapeutic benefit is meant eradication or amelioration of the underlying disorder (e.g., skin lesion) being treated and/or eradication or amelioration of one or more of the symptoms associated with the (disorder e.g., pain, discomfort, ischemia, etc.) such that the patient reports an improvement in feeling or condition, notwithstanding that the patient may still be afflicted with the underlying disorder.

For example, administration of a compound to lesion(s) on a patient suffering from a form of diabetes or sickle cell anemia provides therapeutic benefit not only when the dermal lesion is eradicated or ameliorated, but also when the patient reports a decrease in the severity or duration of the symptoms associated with the lesion. Therapeutic benefit also includes halting or slowing the progression of the disease (e.g., slowing or stopping the increase in size of a lesion, or decreasing its size), regardless of whether improvement in symptoms is realized.

The amount of non-acidified sodium nitrite administered will depend upon a variety of factors, including, for example, the particular condition being treated, the mode of administration, the severity of the condition being treated (specifically, the area/size of the lesion to which the composition is applied), the age of the patient, etc. Determination of an effective dosage is well within the capabilities of those skilled in the art, though guidelines are provided herein (e.g., in Examples 1 and 2). A skilled practitioner will be able to determine the optimal dose for a particular individual, condition, or lesion.

In cases of local administration, such as local topical administration, the effective local concentration of active compound(s) may not be related to plasma concentration. Skilled artisans will be able to optimize effective local dosages without undue experimentation. In view of the much higher therapeutic index of topical administration to the skin, dosages can be increased beyond general systemic dosages without significant additional concern for side-effects and toxicities. For topical administration, effective dosages may be those where no significant systemic circulation of the compounds results from administration to the skin or eye, for example, where a topical formulation is applied directly to a cutaneous lesion and a localized dose is utilized.

In particular embodiments, the topical non-acidified sodium nitrite compound/formulation is administered to a subject once daily, twice daily, three times daily, once every two days, once weekly, twice weekly, three times weekly, once biweekly, once monthly, or once bimonthly. In certain embodiments, the compound is administered to the subject twice a week. Administration may continue for any defined time, or for an indefinite period, for instance until a certain clinical outcome is reached (e.g., reduction of the size of a wound/ulcer, including but not limited to full closure of the breakage of the skin/dermis).

By way of example, the topical non-acidified sodium nitrite may be applied to an area of skin surface at a rate based on the area to be treated. For instance, a non-acidified sodium nitrite formulation (e.g. a cream or ointment) may be applied at a rate of 0.1 cm of the formulation (dispensed from a tube with a 6.8 mm orifice) for each $cm^2$ of wound surface area, with the formulation applied in an even layer over the treated area. By way of example, using representative formulations presented herein, the amount of sodium nitrite contained in 1 cm (by 6.8 mm diameter) of the 0.5%, 1%, 1.5%, 1.8%, and 2% cream/ointment formulations is 1.38 mg, 2.75 mg, 4.13 mg, 4.95 mg, and 5.50 mg, respectively. Thus, 0.1 cm of the same formulations contains 138 µg, 275 µg, 413 µg, 495 µg, and 550 µg, respectively. Representative unit dosages are therefore from about 100 µg to 1 mg per $cm^2$ of surface area to be treated per topical application.

VII. Topical Formulations/Preparations

Provided herein are data demonstrating that non-acidified sodium nitrite, in a topical cream/ointment preparation, is effective for treating skin lesions.

For topical administration, the non-acidified sodium nitrite may be formulated as a solution, gel, ointment, cream, suspension, etc., which formulation types are well-known in the art. One embodiment is a pharmaceutical formulation comprising non-acidified sodium nitrite, where the formulation is selected from a solution, a gel, an ointment, a cream and a suspension. In one aspect, such formulations formulated for topical administration include a therapeutically effective amount of non-acidified sodium nitrite or a pharmaceutically acceptable salt thereof. A person of skill in the art will appreciate that a therapeutically effective amount of the compound may vary, but typically the therapeutically effective amount is from 0.1% to 10% (w/w), for instance from 0.5% to 3%, 1% to 3%, 1.5% to 2%, or more specifically 0.5%, 1%, 1.5%, 1.8%, or 2% (w/w).

Typically, the sodium nitrite preparations provided herein are non-acidified, as it has surprisingly been found that acidification is not necessary to generate the wound/lesion-healing effects demonstrated herein. In some embodiments, the non-acidified sodium nitrite preparation is produced by dissolving sodium nitrite powder in water to produce a (relatively) concentrated sodium nitrite solution, then dispersing an amount of that aqueous solution in a volume of topical base, such as a petrolatum product (e.g., white petrolatum ointment). Optionally, the sodium nitrite powder can be dissolved in a normal saline solution such as a physiologically buffered saline solution or buffered water. Specific non-limiting examples of the carriers and/or diluents that are useful in the pharmaceutical formulations of the present disclosure include water and physiologically acceptable buffered saline solutions, such as phosphate buffered saline solutions. Merely by way of example, the buffered solution can be at a pH of about 6.0-8.5.

In certain embodiments, the topical formulations are formulated for the treatment of skin diseases and/or disorders, such as burns, chronic or acute lesions, including skin lesions associated with sickle cell anemia, diabetes, decubitus wounds. More generally, the formulations described herein are expected to be useful for any wounds or skin breakages, where it would be beneficial to increase the flow of blood to the area; to provide non-acidified sodium nitrite as a localized, topical source of nitric oxide; to reduce pain or the perception of pain; and/or to reduce microbial growth.

The pharmaceutical formulation may also comprise a therapeutically effective amount of an additional or subsequent active agent, or agents. Certain disclosed embodiments of the pharmaceutical formulation comprise a therapeutically effective amount of an additional or subsequent agent suitable for treating a skin breakage or lesion, such as a topical antibiotic or anti-inflammatory.

The pharmaceutical compositions for the administration of non-acidified sodium nitrite as provided herein may conveniently be presented in dosage unit form and may be prepared by any of the methods well known in the art of pharmacy. The pharmaceutical compositions can be, for example, prepared by uniformly and intimately bringing the active ingredient into association with a liquid carrier or a finely divided solid carrier or both, and placing it in appropriate packaging. For example, in topical formulations of the disclosed compounds, the formulation is placed in an appropriate container (such as a squeeze-tube with a cap for dispensing ointments and creams). Alternatively, the dispenser may include a device for dispensing unit dosages of the drug (such as a bottle or dropper that dispenses a controlled pre-determined dosage of the drug to a target area). In the pharmaceutical composition, non-acidified sodium nitrite is included in an amount sufficient to produce the desired therapeutic effect.

The formulations may have preservatives or be preservative-free (for example in a single-use container). One embodiment is any of the aforementioned formulations in a kit for topical or local administration.

The pharmaceutical formulations also may include a penetration enhancer, such as dimethyl isosorbide, propylene glycol, and combinations thereof; an emollient, such as water; a surfactant, such as sorbitan monostearate, a polyethylene glycol monostearate, D-α-tocopheryl polyethylene glycol 1000 succinate, a composition comprising glycol stearate/PEG32 stearate/PEG6 stearate, and combinations of surfactants; an antioxidant, such as butylated hydroxyanisole, butylated hydroxytoluene, ascorbic acid, a tocopherol, and combinations thereof. The pharmaceutical formulation may comprise other agents, such as a fragrance, an absorbent, an astringent, a binder, a buffering agent, a chelating agent, a film-forming agent, a conditioning agent, an opacifying agent, a protectant, or any combination thereof.

Topical formulations comprising non-acidified sodium nitrite optionally may comprise additional pharmaceutically acceptable ingredients such as solvents, topical bases, surfactants/emulsifiers, penetration enhancers, emollients, antioxidants, color additives diluents, stabilizers, adjuvants, and any combination thereof. Methods of formulating and testing drugs for topical application are described, for example, in Remington, The Science and Practice of Pharmacy ($21^{st}$ edition), pages 872-882 (2006).

Topical bases include, but are not limited to, hydrophobic vehicles such as hydrocarbons, liquid petrolatum (mineral oil, liquid paraffin, paraffin oil), white petrolatum (petroleum jelly, VASELINE®), yellow petrolatum (petroleum jelly), squalane (perhydrosqualene, spinacane), and silicones; silicones such as liquid polydimethylsiloxanes (dimethicone, silastic, medical grade silicone oil), alcohols such as lauryl alcohols (1-dodecanol, dodecyl alcohols), myristyl alcohols (tetradecanol, tetradecyl alcohols), cetyl alcohols (hexadecanol, ethal, palmityl alcohols), stearyl alcohols (stenol, cetosteryl alcohols), oleyl alcohols (ocenol); sterols such as sterol esters; lanolin such as hydrous wool fat, lanum; anhydrous lanolin (such as wool fat, anhydrous lanum, agnin); semi synthetic lanolins; carboxylic acids such as lauric acid, myristic acid, palmitic acid, stearic acid, oleic acid; esters and polyesters, such as cholesterol esters (stearate), ethylene glycol monoesters, propylene glycol monoesters, glyceryl monoesters, glyceryl monostearate, sorbitol monoesters, sorbitan monoesters, sorbitol diesters, sorbitan polyesters (spans, arlacels), glyceryl tristearate, lard, almond oil, corn oil, castor oil, cottonseed oil, olive oil, soybean oil, hydrogenated oils, sulfated oils, isopropyl myristate, isopropyl palmitate; and ethers and polyethers (polydisperse or monodisperse), such as polyethylene glycols or polypropylene glycols (pluronics).

Additional contemplated ingredients include ceresin, panthenol, and bisabolol.

Water-miscible solvents that may be used include polyols and polyglycols such as propylene glycol (1,2-propanediol), glycerin (glycerol), liquid polyethylene glycol, solid polyethylene glycol (hard macrogol, Carbowax®), glycol furol, 1,2-phenol-hexanetriol, sorbitol solution, esters and polyesters such as polyoxyethylene sorbitan monoesters (e.g., Tween® 60) and polyoxy ethylene sorbitan polyesters (e.g., Tween® 20), ethers and polyethers such as polyethylene glycol monocetyl ether (cetomacrogol 1000) and polyethylene-polypropylene glycols (pluronics). In one embodiment, the water-miscible solvent includes PEG-400. Surprisingly, use of standard GMP quality PEG-400 was found to introduce impurities into the formulation. Without being limited to any particular theory it currently is believed that trace amounts of formaldehyde in the PEG-400 reacted with compound I. Disclosed herein are formulations including PEG-400 substantially free of impurities, such as PEG-400 having less than about 65 ppm formaldehyde, such as less than about 10 ppm formaldehyde or about 1 ppm or less formaldehyde.

Suitable surfactants include, but are not limited to a sterol or sterol ester, for example cholesterol (cholesterin), lanolin (hydrous wool fat, lanum), anhydrous lanolin (wool fat, anhydrous lanum, agnin), or semi synthetic lanolin; carboxylic acids such as $Na^+$, $K^+$, ethanolamine salts of lauric acid, myristic acid, palmitic acid, stearic acid, oleic acid, or an ether or polyether such as polyethylene-polypropylene glycols (pluronics). If an oil-in-water (o/w) emulsifier is desired, the following examples may be used: esters and polyesters such as polyoxyethylene, sorbitan monoesters (Span™ 20, Span™ 40, Span™ 80), polyoxy ethylene esters (stearate-polyethylene glycol monoesters, Myrj® 45, Myrj® 59), polyoxy ethylene sorbitan polyesters (tweens); ethers and polyethers such as polyethylene glycol monocetyl ether (cetomacrogol 1000) or polyethylene-polypropylene glycols (pluronics), and others such as sodium lauryl sulfate, borax (sodium borate), ethanolamine, or triethanolamine. Nonionic surfactants, like Surfactant 190 (dimethicone copolyol), Polysorbate 20 (Tween® 20), Polysorbate 40 (Tween® 40), Polysorbate 60 (Tween® 60), Polysorbate 80 (Tween® 80), lauramide DEA, cocamide DEA, and cocamide MEA, amphoteric surfactants like oleyl betaine and cocamidopropyl betaine (Velvetex® BK-35), and cationic surfactants, like Phospholipid PTC (Cocamidopropyl phosphatidyl PG-dimonium chloride), can be used. Appropriate combinations or mixtures of such surfactants may also be used.

Penetration enhancers improve drug delivery into the skin. Suitable penetration enhancers include, but are not limited to, alcohol, alkyl methyl sulfoxide, pyrrolidone, laurocapram, dimethyl formamide, tetrahydrofurfuryl alcohol, an amphiphile, or other miscellaneous enhancers such as clofibric acid amide, hexamethylene lauramide, dimethyl isosorbide, propylene glycol, proteolytic enzymes, terpenes or sesquiterpenes.

Suitable moisturizers for use in the formulations of compound I include, but are not limited to, lactic acid and other hydroxy acids and their salts, glycerin, propylene glycol, butylene glycol, sodium PCA, Carbowax® 200, Carbowax® 400, and Carbowax® 800. Suitable emollients for use in the formulations include, but are not limited to, water, PPG-15 stearyl ether, lanolin alcohol, lanolin, lanolin derivatives, cholesterol, petrolatum, isostearyl neopentanoate, octyl stearate, mineral oil, isocetyl stearate, Ceraphyl® 424 (myristyl myristate), octyl dodecanol, dimethicone (Dow Corning 200-100 cps), phenyl trimethicone (Dow Corning 556), Dow Corning 1401 (cyclomethicone and dimethiconol), and cyclomethicone (Dow Corning 344), and Miglyol® 840 (manufactured by Huls; propylene glycol dicaprylate/dicaprate). In addition, appropriate combinations and mixtures of any of these moisturizing agents and emollients may be used.

The composition may also include preservatives, antimicrobials, and/or antioxidants, such as benzalkonium chloride, benzoic acid, benzyl alcohol, bronopol, chlorhexidine, chlorocresol, imidazolidinyl urea, paraben esters, phenol, phenoxyethanol, potassium sorbate, or sorbic acid; antioxidants such as α-tocopherol (vitamin E), tocotrienol, ascorbic acid, ascorbyl palmitate, butylated hydroxyanisole, butylated hydroxytoluene, sodium ascorbate, sodium metabisulfite; chelating agents such as citric acid or edetic acid; buffers such as citric acid and salts, phosphoric acid and salts, $H_3PO_4/NaH_2PO_4$, glycine, acetic acid, triethanolamine, or boric acid; humectants such as glycerin (glycerol), propylene glycol (E1520), glyceryl triacetate (E1518), sorbitol (E420), xylitol and malitol (E965), polydextrose (E1200), quillaia (E999), lactic acid, urea or lithium chloride; and/or a sequestering antioxidant such as citric acid and it salts ethylenediaminetetraacetic acid (Versene®, EDTA).

The composition further may include dyes/colorants and/or fragrances. Suitable fragrances and colors, such as caramel, FD&C Red No. 40 and FD&C Yellow No. 5, may be used in the formulations. Other examples of fragrances and colors suitable for use in topical products are known in the art.

Other suitable additional and adjunct ingredients which may be included in the formulations include, but are not limited to, absorbents (e.g., hydrogels), astringents (e.g., witch hazel, alcohol, and herbal extracts such as chamomile extract), binders (e.g., starch, cellulose ethers, microcrystalline cellulose, calcium hydrogen phosphate, calcium phosphate dibasic, and calcium sulfate dihydrate), other excipients (e.g., polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose), buffering agents (e.g., monobasic or dibasic potassium phosphate, monobasic or dibasic sodium phosphate, magnesium hydroxide), chelating agents (e.g., EDTA (ethylenediaminetetraacetic acid, tetrasodium salt)), film-forming agents (e.g., chitosan, hydroxypropylmethylcellulose, polyvinyl alcohol), conditioning agents (e.g., petrolatum, glycerin, propylene glycol), opacifying agents (e.g., titanium dioxide), pH adjusters (e.g., citric acid and sodium hydroxide), and protectants. Examples of each of these ingredients, as well as examples of other suitable ingredients in topical product formulations, may be found in publications by The Cosmetic, Toiletry, and Fragrance Association (CTFA). See, e.g., CTFA Cosmetic Ingredient Handbook, 2nd edition, eds. John A. Wenninger and G. N. McEwen, Jr. (CTFA, 1992).

A particular embodiment of the topical treatment may be an ointment, which is a semisolid preparation intended for external application to the skin or mucous membranes. In a specific example, the ointment is based on petrolatum. The ointment does not contain sufficient water to separate into a second phase at room temperature. A water-soluble ointment may be formulated with polyethylene glycol. Ointments are ideal emollients with good skin penetration and adherence to surfaces. The ointment is in a convenient container such as a tube or jars.

Alternatively, the topical dosage form is a cream in which the compounds are dissolved or suspended in water removable or emollient bases. The creams may be either water-in-oil or oil-in-water compositions Immiscible compounds may be combined by mechanical agitation or heat using wet gum, dry gum, bottle, and beaker methods. In some embodiments, the cream is an oil-in-water emulsion or aqueous microcrystalline dispersion of long chain fatty acids or alcohols that are water washable and more cosmetically and aesthetically acceptable.

In other embodiments, the active ingredient(s) are provided for administration in a paste, which can be considered an ointment into which a high percentage of insoluble solids have been added, for example as much as 50% by weight. The paste is much stiffer than the ointment due to the presence of solids, which form a particulate matrix over and above the ointment structure already present. Ingredients such as starch, zinc oxide, calcium carbonate, and talc are used as the solid phase. Pastes provide a particularly good protective barrier on skin. Like ointment, a paste forms an unbroken, relatively water impermeable film on the skin surface; unlike ointment the film is opaque and therefore an effective sun filter. Thus, pastes are particularly effective for protecting the skin from ultraviolet radiation that may worsen the condition being treated.

In yet other embodiments, the active agent is provided in a gel, jelly or lotion. Gels are semisolid systems consisting of dispersions of small or large molecules in an aqueous liquid vehicle rendering jelly-like through the addition of gelling agent. Among the gelling agents used are synthetic macromolecules, such as carbomer 934, and cellulose derivatives, such as carboxymethylcellulose or hydroxypropylmethyl-cellulose. Gels are compatible with many substances and may contain penetration enhancers to improve delivery into the skin. The gels may be either single-phase gels in which the macromolecules are uniformly distributed throughout a liquid with no apparent boundaries between the dispersed macromolecules and the liquid, or double-phase gels in which the gel mass consists of floccules of small distinct particles, often referred to as a magmas. A jelly contains a water-soluble base prepared from natural gums such as tragacanth, pectin, alginate, or boroglycerin, or from synthetic derivatives of a natural substance such as methylcellulose or carboxymethylcellulose. A lotion is a clear solution containing 25-50% alcohol, which optionally contains an antiseptic, or mollient. Other optional ingredients that may be added to the lotion are an extract of witchhazel, menthol, glycerin, boric acid, alum, or potassium oxyquinoline.

Other methodologies and materials for preparing formulations in a variety of forms are also described in Anthony L. L. Hunting (ed.), "A Formulary of Cosmetic Preparations (Vol. 2)—Creams, Lotions and Milks," Micelle Press (England, N.J. 1993). See, for example, Chapter 7, pp. 5-14 (oils and gels); Chapter 8, pp. 15-98 (bases and emulsions); Chapter 9, pp. 101-120 ("all-purpose products"); Chapter 10, pp. 121-184 (cleansing masks, creams, lotions); Chapter 11, pp. 185-208 (foundation, vanishing and day creams); Chapter 12, pp. 209-254 (emollients); Chapter 13, pp. 297-324 (facial treatment products); Chapter 14, pp. 325-380 (hand products); Chapter 15, pp. 381-460 (body and skin creams and lotions); and Chapter 16, pp. 461-484 (baby products).

Embodiments of the disclosed pharmaceutical compositions may be used in an application device that permits application of the composition to a target site on the skin without applying the composition to non-target site areas of the skin. For example, a device may be employed that allows the composition to be applied without first applying the composition to one's fingers. Suitable devices include spatulas, swabs, syringes without needles, and adhesive patches. Use of spatulas or swabs, or the like may require the device to be inserted into a container containing the composition. Using syringes or adhesive patches may be accomplished by filling the syringe or patch with the composition. The composition may then be topically spread by the spatulas or swabs, or may be expelled from the syringes onto the person's skin.

IX. Co-Administration

When used to treat lesions of the skin and/or mucous membranes, non-acidified sodium nitrite may be administered singly or in combination with other agents useful for treating diseases and/or disorders of the skin. Non-acidified sodium nitrite may be administered in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, -agonists, tryptase inhibitors, aspirin, cyclooxygenase (COX) inhibitors, methotrexate, anti-TNF drugs, rituxan, PD4 inhibitors, p38 inhibitors, PDE4 inhibitors, arginase inhibitors, antioxidants, and antihistamines, to name a few.

The pharmaceutical compositions disclosed herein can be co-administered (concurrently or sequentially) with a variety of other treatments applied to the skin, for example antibacterials (such as BACTROBAN® or CLEOCIN®); antipsoriasis medications (such as Micanol®); antifungal agents (such as LAMISIL®, LOTRIMIN®, and NIZORAL®); acne treatments (such as benzoyl peroxide topical preparations); treatments for seborrheic dermatitis (such as coal tar); corticosteroids; retinoids (such as Retin-A and Tazorac®) which are gels or creams derived from vitamin A that are used to treat conditions including acne; and wart treatments (such as salicylic acid). Any of these agents can be provided in topical or cosmetic formulations, for example in lotions, ointments, creams, gels, soaps, shampoos, or adherent applicators, such as patches.

The pharmaceutical compositions disclosed herein can also be co-administered (concurrently or sequentially) with a variety of other treatments that are not applied to the skin, for example treatments that are administered systemically, for example orally or parenterally. Examples of such systemic treatments include other anti-lupus drugs (such as hydroxychloroquine (PLAQUENIL®), corticosteroids (such as Prednisone), antibiotics (such as erythromycin, tetracycline, and dicloxacillin), antifungal agents (such as ketoconazole and DIFLUCAN®), antiviral agents (such as VALTREX®, acyclovir, and FAMVIR®), corticosteroids, immunosuppressants (such as CYTOXAN®, azathioprine, methotrexate, mycophenolate), and biologics (such as RITUXAN®, ENBREL®, HUMIRA®, REMICADE®, STELARA®, and AMEVIVE®).

Particular immunosuppressive therapies that can be used in combination with non-acidified sodium nitrite include, for example, mercaptopurine, corticosteroids such as prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies, for example, antilymphocyte globulin (ALG), antithymocyte globulin (ATG), monoclonal anti-T-cell antibodies (OKT3) and irradiation. These various agents can be used in accordance with their standard or common dosages, as specified in the prescribing information accompanying commercially available forms of the drugs (see also, the prescribing information in the 2006 Edition of *The Physician's Desk Reference*), the disclosures of which are incorporated herein by reference. Azathioprine is currently available from Salix Pharmaceuticals, Inc. under the brand name AZASAN®; mercaptopurine is currently available from Gate Pharmaceuticals, Inc. under the brand name PURINETHOL®; prednisone and prednisolone are currently available from Roxane Laboratories, Inc.; methyl prednisolone is currently available from Pfizer; sirolimus (rapamycin) is currently available from Wyeth-Ayerst under the brand name RAPAMUNE®; tacrolimus is currently available from Fujisawa under the brand name PROGRAF®; cyclosporine is current available from Novartis under the brand dame SANDIMMUNE® and Abbott under the brand name GENGRAF®; IMPDH inhibitors such as mycophenolate mofetil and mycophenolic acid are currently available from Roche under the brand name CELLCEPT® and Novartis under the brand name MYFORTIC®; azathioprine is currently available from Glaxo Smith Kline under the brand name IMURAN®; and antibodies are currently available from Ortho Biotech under the brand name ORTHOCLONE®, Novartis under the brand name SIMULECT® (basiliximab) and Roche under the brand name ZENAPAX® (daclizumab).

Also contemplated is treatment with a preparation containing CpG oligonucleotides useful in accelerating wound healing, such as those described in PCT Publication WO 2013/162828, which is herein incorporated by reference.

The following examples are provided to illustrate certain particular features and/or embodiments. These examples should not be construed to limit the disclosure to the particular features or embodiments described.

EXAMPLES

Example 1: Topical Sodium Nitrite Formulation

This example provides an overview of embodiments of the non-acidified sodium nitrite preparation described herein, which is useful in the topical treatment of skin lesions such as ulcers.

Product Description:

Sodium nitrite 0.5, 1, 1.5, 1.8, 2, 2.5 and 3.0% formulations were compounded by dissolving sodium nitrite powder in a small volume of water to yield a sodium nitrite concentration of 30%, followed by filter sterilization of the aqueous solution of sodium nitrite through a 0.22 micron filter. The filtered aqueous solution of sodium nitrite was then thoroughly dispersed into AQUAPHOR™ ointment (Beiersdorf AG). The volume of the aqueous solution dispersed into the white petrolatum ointment was about 4-5% v/w. The 0.5% composition consists of 0.005 g of sodium nitrite powder in 1 g of AQUAPHOR™ ointment and was dispensed in multiuse 30 g tubes with a 6.8 mm dispensing orifice. The 1, 1.5, 1.8, 2, 2.5, and 3.0% formulations consist of 0.01, 0.015, 0.018, 0.02, 0.025, and 0.03 g of sodium nitrite, respectively, in 1 g of AQUAPHOR™ ointment and are dispensed in 30 g tubes. The amount of sodium nitrite contained in 1 cm of ointment (extruded through the 6.8 tube mm orifice) for the 0.5, 1, 1.5, 1.8, 2, 2.5, and 3.0% formulation is 1.38, 2.75, 4.13, 4.95, 5.50, 6.88, and 8.26 mg, respectively.

Storage:

Stored at 2° C.-8° C. in the refrigerator in tubes coated with TEFLON'.

Stability:

Stable for at least four years at controlled room temperature (15-30° C.) or refrigerated (2-8° C.).

Route of Administration:

Applied topically to the ulcerated area and covered by dressing two times a week. The sodium nitrite formulation was applied using a sterile spatula over the wound in a thin layer. The proportion of the sodium nitrite composition used was 0.1 cm (extruded through the 6.8 mm tube orifice) per $cm^2$ of surface area.

Example 2: Topical Sodium Nitrite for Chronic Leg Ulcers in Patients with Sickle Cell Anaemia: a Phase 1 Dose-Finding Safety and Tolerability Trial This example describes a Phase I study using various dose levels of non-acidified sodium nitrite ointment to treat chronic leg ulcers in sickle cell anemia patients. Material in this example was published as Minniti et al., *Lancet Haematol* 1:3-95-103, Nov. 13, 2014.

Brief Synopsis

Background

Well-tolerated and effective treatments are needed for chronic leg ulcers in sickle cell anaemia. Topical sodium nitrite, a known nitric oxide donor, enhances blood flow in ulcers and has known bacteriostatic effects. This study aimed to assess the safety, tolerability, and pharmacokinetics of topical sodium nitrite in patients with sickle cell disease and chronic leg ulcers.

Methods

Adult patients from an ambulatory clinic at the National Institutes of Health (Bethesda, Md., USA) with sickle cell anaemia with leg ulcers (with a surface area of 2.5-100 cm$^2$) persisting for at least 4 weeks were enrolled into a safety and tolerability phase 1 dose-escalation trial of topical sodium nitrite. Increasing concentrations of sodium nitrite cream were applied twice weekly for 4 weeks to one ulcer per patient at five dose levels (0.5%, 1%, 1.5%, 1.8%, and 2%). The primary endpoints were safety and tolerability, with secondary endpoints of pharmacokinetics, blood flow, and wound healing. Pain relief was analysed post hoc. Endpoints were analysed over time for the whole study population and according to dose level. This study is registered with ClinicalTrials.gov, number NCT01316796 (incorporated herein in its entirety).

Findings

Between Apr. 4, 2011, and Mar. 19, 2013, 18 adult patients with sickle cell anaemia and leg ulcers were enrolled into this trial. Three patients were assigned into each cohort, and each cohort was treated with a different concentration of sodium nitrite cream (cohort 1: 0.5%, cohort 2: 1.0%, cohort 3: 1.5%, and cohort 4: 2.0%). Patients were not enrolled into the next cohort dose until it was established that no dose-limiting toxicities were observed. Six additional patients were enrolled to cohort 3a: 1.8%, after two patients in cohort 4 had asymptomatic drops in diastolic blood pressure.

No grade 3-4 adverse events were observed, and there were no serious adverse events or dose-limiting side-effects. Pharmacokinetic analysis showed that systemic absorption of sodium nitrite was very low. Application of topical sodium nitrite was associated with a significant increase in periwound cutaneous blood flow measured by laser speckle contrast imaging (p=0.0002), corroborated by increased periwound skin temperature by infrared thermography (p=0.0119). Dose-dependent decreases in leg ulcer size (p=0.0012) and pain (p<0.0001) were recorded. Ulcers healed completely in three patients who received the highest concentrations of topical sodium nitrite (the 1.8% and 2% cream). In the post-hoc analysis of pain, brief pain inventory scores improved in pain severity (p=0.0048) and pain interference (p=0.0013).

Interpretation

These results indicate that topical sodium nitrite, such as 2% cream (ointment), is suitable for use in adults with sickle cell anaemia to promote healing of leg ulcers.

Introduction

Morbidity from chronic leg ulcers remains a substantial clinical burden in patients with sickle cell disease, despite advances in care including the use of disease-modifying agents such as hydroxycarbamide and blood transfusions, and improved supportive care (Minniti et al., *Am J Hematol.*; 86: 705-708, 2011). Patients with sickle cell disease and leg ulcers have biomarkers of more severe haemolytic anaemia, a state associated with low bioavailability of nitric oxide. Existing therapeutic approaches for sickle cell disease ulcers are unsatisfactory, and are mostly based on treatments for venous and arterial ulcers in the general population. A recent Cochrane review (Marti-Carvajal et al., *Cochrane Database Syst Rev.*; 11 (CD008394) 2012) identified only six prospective, randomised therapeutic trials in sickle cell disease leg ulcers in the past 30 years—four in Jamaica (Baum et al., *Trans R Soc Trop Med Hyg.*; 81: 847-849, 1987; Serjeant et al., *J Am Acad Dermatol.*; 37: 491-493, 1997; Serjeant et al., *West Indian Med J.*; 26: 164-166, 1977; La Grenade et al., *West Indian Med J.*; 42: 121-123, 1993) and two in the USA (Wethers et al., *Blood.*; 84: 1775-1779, 1994; McMahon et al., *Br J Haematol.*; 151: 516-524, 2010). The results were mixed, with statistically significant increases in wound closure reported with topical Arg-Gly-Asp (RGD) peptide (Wethers et al., *Blood.*; 84: 1775-1779, 1994) and intravenous arginine butyrate (McMahon et al., *Br J Haematol.*; 151: 516-524, 2010). These agents remain in early-phase drug development, and patients have few therapeutic options available (Delaney et al., *Hemoglobin*; 37: 325-332, 2013). Sodium nitrite was selected for clinical development on the basis of the extensive published literature about its safety profile when administered intravenously (Dejam et al., *Circulation.*; 116: 1821-1831, 2007; Mack et al., *Br J Haematol.*; 142: 971-978, 2008) and orally (Greenway et al., *Diabetes Technol Ther.*; 14: 552-560, 2012), its vasodilating properties (Dejam et al., *Circulation.*; 116: 1821-1831, 2007; Mack et al., *Br J Haematol.*; 142: 971-978, 2008; Tucker et al., *Lancet.*; 354: 1670-1675, 1999; Phillips et al., *Antimicrob Agents Chemother.*; 48: 2866-2870, 2004), and preliminary reports of acidified nitrite in other patient populations with chronic skin ulcers (Tucker et al., *Lancet.*; 354: 1670-1675, 1999; Phillips et al., *Antimicrob Agents Chemother.*; 48: 2866-2870, 2004).

In animals, sodium nitrite has been shown to promote revascularisation of ischaemic limbs; to protect against ischaemic infarction of the heart, liver, and brain; and to have a protective effect against cardiac arrest-mediated heart and brain injury (Shiva & Gladwin, *Basic Res Cardiol.*; 104: 113-119, 2009). The nitrite anion acts as a vasodilator in vivo by generating nitric oxide in tissues with low oxygen tension and pH (Shiva & Gladwin, *Basic Res Cardiol.*; 104: 113-119, 2009; Schwentker & Billiar, *Surg Clin North Am.*; 83: 521-530, 2003), which are conditions that are likely to be present in chronic wounds. The mechanism involves an oxygen-dependent and pH dependent nitrite reductase activity of haemoproteins or xanthine oxidoreductase (Shiva & Gladwin, *Basic Res Cardiol.*; 104: 113-119, 2009; Schwentker & Billiar, *Surg Clin North Am.*; 83: 521-530, 2003). Experimental models have suggested beneficial effects of nitric oxide in the early and late phases of wound healing, including increased extracellular matrix production, immune response modulation, and stimulation of keratinocyte cell proliferation, angiogenesis, and bactericidal properties (Luo et al., *Acta Pharmacol Sin.*; 26: 259-264, 2005; Schwentke et al., *Nitric Oxide.*; 7: 1-10, 2002; Fang, *J Clin Invest.*; 99: 2818-2825, 1997; Bulgrin et al., *Wounds.*; 7: 48-57, 1995; Kirk et al., *Surgery.*; 114: 155-160, 1993;

Contreras et al., *Pharmacol Ther.*; 112: 553-563, 2006; Jones et al., *Appl Microbiol Biotechnol.*; 88: 401-407, 2010). Nitric oxide mediates essential vascular homoeostasis, including vasodilation, and antiplatelet activity, and affects several growth factors involved in endothelial homoeostasis (Tousoulis et al., *Curr Vasc Pharmacol.*; 10: 4-18, 2012).

Methods

Study Design and Patients

In this single-center, open-label, phase 1 study of increasing doses of sodium nitrite cream, patients 18 years of age and older with confirmed sickle cell disease and a leg ulcer present for at least 4 weeks with a surface area greater than 2.5 $cm^2$ but smaller than 100 $cm^2$ were eligible for inclusion. Patients were recruited from the ambulatory clinic at the Clinical Center of the National Institutes of Health (NIH), National Heart Lung and Blood Institutes (Bethesda, Md., USA). Hydroxycarbamide and chronic transfusions were allowed. Patients with acute infections were excluded. The following is full list of the exclusion criteria:

Exposure to therapeutic nitric oxide, L-arginine, nitroprusside or nitroglycerine within the previous 1 week.

Patients presenting with clinically diagnosed bacterial infection (e.g., osteomyelitis, pneumonia, sepsis or meningitis).

Patients who have a pre-existing methemoglobinemia (more than 2.5%)

Patients who are currently enrolled in any other investigational drug study (this does not include observational or natural history protocols).

Use of PDE5 inhibitors, such as sildenafil, 4 days prior to screening.

Pregnant women (urine or serum HCG+) or nursing mothers.

Originally, it was planned to enroll four cohorts with three patients in each, to give a total of 12 participants. A cream containing four different increasing concentrations of sodium nitrite (0.5% for patients in cohort 1, 1.0% in cohort 2, 1.5% in cohort 3, and 2.0% in cohort 4) was applied twice weekly to one ulcer (the study ulcer) per patient for 4 weeks (eight applications). The first two doses of cream were administered as inpatients, and the remaining six doses in the outpatient day hospital at the NIH Clinical Center. Around four days later, patients returned to the outpatient clinic for removal of the cream and end of study assessments, so the total duration of the study was about 32 days per cohort, which the US Food and Drug Administration judged to be sufficient to assess the safety and pharmacokinetics of sodium nitrite. All three patients in each cohort were assessed for the 32-day duration of the study to ensure no dose-limiting toxicities before patients were enrolled into the next cohort. After 12 participants had been enrolled and treated, we noted occasional asymptomatic, self-resolving decreases in diastolic blood pressure below the predetermined limit of 50 mm Hg, in two patients in cohort four (the 2% sodium nitrite cream cohort). To further assess the safety of the cream, we enrolled an additional six participants (cohort 3a) who received cream containing an intermediate dose of 1.8% sodium nitrite, to create a total of 18 participants. It was planned that participants were to be removed from the study if they experienced dose-limiting toxicities or progression of the ulcer to more than 50% of initial size, and the sodium nitrite dose was to be reduced if the ulcer size decreased by more than 50% of initial size. Toxicity was monitored with clinical laboratory testing at the time of each twice-weekly treatment in the first 12 patients, and weekly for the final six patients who were treated with 1.8% sodium nitrite, including methaemoglobin levels, complete blood counts, and comprehensive serum chemistry panels of liver and kidney function.

All patients were provided written informed consent in accordance with the Declaration of Helsinki to a clinical research protocol approved by the Institutional Review Board of the National Heart, Lung and Blood Institute.

Procedures

In patients with more than one ulcer, all ulcers were treated similarly with standard wound care, with the application of sodium nitrite cream only to the study ulcer. The following was the prospectively defined wound care procedure used in all protocol patients:

Cleanse leg with skin cleanser

Cleanse ulcer with normal saline & gauze removing any debris from wound bed.

Apply petrolatum-based ointment to moisturize under wrap

Cover ulcer with MEPILEX® white foam dressing

Apply two-layer compression wrap to leg (depending on the condition of the ulcer)

Change dressing twice weekly

The study ulcer was selected by the wound care nurse and principal investigator on the basis of ulcer duration, size, and accessibility for digital imaging. Patients completed a brief pain inventory and a 7-day diary of opioid use the week before and after completion of treatment, and identified the areas contributing to their pain. Patients were admitted to hospital (at the NIH Clinical Center) for the first two applications of topical sodium nitrite, and stayed in hospital from Monday morning to Friday afternoon (i.e., for 4.5 days), to help pharmacokinetic sampling and clinical monitoring; thereafter, they were treated in the outpatient clinic (the NIH Clinical Center Day Hospital) twice weekly for 3 further weeks. Sodium nitrite cream was applied on day 3 and day 5 of week 1 at the same time (normally around 10:00 h). Patients were not confined to their bed except for 6-8 h on day 3 when most of the pharmacokinetic sampling and imaging was done. A visual analogue scale pain score was obtained at each treatment during the study (i.e., a total of eight times) for the study ulcer and each of the non-study ulcers. Pain scores were not adjusted for analgesic use. Ulcers were measured manually with a disposable ruler (longest length and widest width) at each encounter and by digital photography three times: before the first application of cream (baseline), and after 2 weeks and after 4 weeks of treatment. ENVI software (version 4.3) was used for digital image analysis of the wound surface area. The ulcer area was calculated by converting the number of pixels representing the ulcer to $cm^2$ using a calibrated square (35.48 mm×35.62 mm×6.52 mm) that was placed near the ulcer for reference. A plain radiograph of the long bones and feet and MRI scan of the lower extremities were obtained to ensure the absence of occult osteomyelitis. Wound cultures were obtained at screening and at the end of the study.

Sodium nitrite cream was compounded and provided by the NIH Clinical Center Pharmacy Department Pharmaceutical Development Section (Bethesda, Md., USA). The amount of sodium nitrite contained in 1 cm of the 0.5%, 1%, 1.5%, 1.8%, and 2% cream was 1.38 mg, 2.75 mg, 4.13 mg, 4.95 mg, and 5.50 mg, respectively. These doses were chosen on safety grounds so that each dose remained well within the intravenous infusion dose already approved by the US Food and Drug Administration for the treatment of cyanide poisoning, in case the sodium nitrite was quickly absorbed systematically. The cream was applied with a sterile spatula over the wound in a thin layer. The proportion of cream used was 0.1 cm of cream for each cm² of wound surface area.

Plasma and whole blood nitrite and nitrate concentrations were collected at the following time points: pre-dose; immediately after application; 5, 10, 15, 20, 30, 45, 60, and 90 min post-dose; 2, 3, 6, 8, 12, 24, and 48 h post-dose; then weekly and at the end of the study. All processing was done at the bedside. Plasma and whole blood nitrite and nitrate were measured with a gas-phase chemiluminescence nitric oxide analyzer, as previously reported (Gladwin et al., *Proc Natl Acad Sci USA.*; 97: 11482-11487, 2000). Methaemoglobin was measured predose, and then 12 times after cream application: immediately afterwards (0 min [baseline]), and then at 15, 30, 45, 60, and 90 min post-application, and 2, 3, 6, 8, 24, and 48 h post-application. Afterwards, for weeks 2-4, met haemoglobin was monitored weekly.

Adverse events were recorded and assessed for their association with the study drug at every encounter and between visits by telephone, and were classified according to the Common Terminology Criteria for Adverse Event standards (CTCAE) version 4.0, 2010. Dose-limiting toxicity included clinically significant hypotension (blood pressure lower than 85/50 mm Hg, and/or symptomatic dizziness, tachycardia, or hypoxia, according to the judgment of the principal investigator). The mean of at least three blood pressure measurements recorded 24 h before the first application of the cream was viewed as the "baseline" value. Pulse oximetry was recorded continuously during inpatient stay and at each outpatient visit.

Digital photographs were taken to measure ulcer surface area and to draw the periwound area—the region of interest—before the first cream application, at week 3, and at the end of the study. The internal and external border of each region of interest was drawn around the ulcer by the image processing toolbox of MATLAB 7.10. The resulting annular region of interest, roughly 1.5-2 cm in size, was used to analyze changes in periwound blood flow and temperature. Images were collected after acclimatization at a room temperature of around 23° C. A calibrated infrared camera (3-5 μm wavelength, temperature resolution of 0.015° C.), measured periwound temperature at a sampling rate of about 1.9 Hz. In conjunction with infrared thermography, a laser speckle contrast imaging camera (moor FLPI Full-Field Laser Perfusion Imager (Moor Instruments Ltd, Wilmington, Del., USA) with flux measurement accuracy of within 10% was used to record red blood cell flux at a sampling rate of about 5 Hz (775-795 nm laser wavelength, 113×152 pixels per image, 16 bits). Infrared cameras were positioned roughly 42 cm from the ulcer and laser speckle contrast imaging cameras were placed about 32 cm from the ulcer.

Outcomes

The primary outcome was the safety and tolerability of topical sodium nitrite. The secondary outcomes were changes in ulcer size and pain (in which pain was analysed post hoc, although all the data were a prospectively obtained at predefined time points), and the pharmacokinetics of topical sodium nitrite cream and methaemoglobin, with exploration of the possible mechanisms of action such as changes in regional blood flow and local temperature after cream application.

Statistical Analysis

We compared laboratory parameters using a pairwise t test. Analyses of the blood pressure considered measurement within 24 h before and after initial cream application; we did two-sample t tests by cohort to assess any differences. Correlation analyses are reported using Spearman's rank correlation coefficient. The statistical significance was set at a two-sided p value lower than 0.05. Analyses were done with R version 2.13.1.

This study is registered with ClinicalTrials.gov, number NCT01316796.

Results

Between Apr. 4, 2011, and Mar. 19, 2013, 23 adult patients with sickle cell anaemia were screened for inclusion, 18 of whom enrolled and completed the trial. Reasons for disqualification of the five patients who were not eligible were enrolment in another trial (one patient) and the ulcer being too small or acutely infected (four patients). Table 1 show the baseline patient demographics and ulcer characteristics. Chronic daily opioid use was almost universal at study entry (16 [89%] of 18 patients) and attributed to localized pain at the ulcer site in 15 patients. Half of the patients were taking hydroxycarbamide and three of 18 (17%) were receiving chronic transfusions. Both treatments are used frequently in adults with sickle cell anaemia disease with several complications, such as the patient population with chronic leg ulcers, as confirmed in a recent survey of treatment patterns for sickle cell disease and ulcers in North America (Delaney et al., *Hemoglobin.*; 37: 325-332, 2013; Trent & Kirsner, *Adv Skin Wound Care.*; 17: 410-416, 2004).

TABLE 1

| Baseline characteristics | |
|---|---|
| | Value |
| Sex | |
| Men | 8 (44%) |
| Women | 10 (56%) |
| Age (years) | 39 (12); range 20-59 |
| Ulcer size (cm²) | |
| Measured manually | 7.50 (4.65); range 2.09-16.50 |
| Measured digitally | 5.97 (3.40); range 2.51-14.66 |
| Number of ulcers | 1.5 (1-3.25) |
| Age of ulcers (months) | 10 (3.75-18.5) |
| Hydroxyurea therapy | 9 (50%) |
| Chronic transfusion | 3 (17%) |
| Taking daily opioid | 16 (89%) |
| Current anti-coagulation therapy | 6 (33%) |
| Hospital admission in past 12 months for vaso-occlusive crisis | 9 (50%) |
| History of priapism (men only) | 5/8 (63%) |
| History of pulmonary embolism or deep vein thrombosis | 8 (44%) |
| Mean arterial pressure (mmHg) | 81.1 (8.2) |
| Systolic blood pressure (mmHg) | 118.6 (13.0) |
| Diastolic blood pressure (mmHg) | 64.0 (7.3) |
| Pulse oximeter on room air | 96.8 (1.1) |
| Previous ulcer treatments per patient | 5 (7-9) |
| Number of patients who had each previous treatment | |
| Surgical/sharp debridement | 18 (100%) |
| Hyperbaric chamber | 7 (39%) |
| Skin graft | 6 (33%) |
| MIST | 4 (22%) |
| Oral/parenteral antibiotics | 11 (61%) |

Data are n (%), mean (SD), or median (IQR), unless otherwise indicated.

A full list of the organisms recovered from cultures at the beginning and at the end of treatment is presented in Table 2. MRI of the lower extremities was done at study entry in 17 of 18 patients (one patient did not have an MRI scan because of the presence of brain surgical clips). One patient had evidence of resolved osteomyelitis. Lower extremity Doppler ultrasound clinical examinations showed one partially resolved venous clot in one patient and a clot in each popliteal vein in a second patient.

TABLE 2

Results of bacterial and fungal cultures of ulcers before and at end of study in each of the subjects.

| Before sodium nitrite cream application | End of Study |
| --- | --- |
| Moderate *Staphylococcus aureus*, moderate *Klebsiella pneumoniae* | Moderate *Staphylococcus aureus*, moderate *Klebsiella pneumoniae*, light *Streptococcus agalactiae* (Group B) |
| Heavy *Staphylococcus aureus*, heavy *Enterococcus faecalis*, scant *Candida albicans* | Heavy *Staphylococcus aureus*, heavy *Enterococcus faecalis* |
| Heavy *Corynebacterium* species | Not collected |
| 1 colony Coagulase-Negative *Staphylococcus* | Heavy *Staphylococcus aureus*, *Streptococcus agalactiae* |
| Heavy Methicillin Sensitive *Staphylococcus aureus* | Moderate Methicillin Sensitive *Staphylococcus aureus* & *Corynebacterium* species |
| Moderate Group B *Streptococcus* | Heavy Group B *Streptococcus*, Moderate Coagulase-Negative *Staphylococcus*, 1 colony *Candida albicans* |
| Moderate *Staphylococcus aureus*/Heavy *Pseudomonas*/Moderate Coagulase-Negative *Staphylococcus* | Moderate *Staphylococus aureus* |
| Skin flora | Skin flora |
| Skin flora | Skin flora |
| Skin flora | Skin flora |
| Moderate *Staphylococcus aureus* | Heavy *Staphylococcus aureus*, Group B *Streptococcus* |
| Moderate *Corynebacterium*, moderate *Staphylococcus aureus* | Heavy *Staphylococcus aureus* |
| Skin flora | No growth |
| *Enterococcus faecalis*, moderate *Candida albicans*. | Skin flora |
| No growth | Skin flora |
| Moderate MRSA, scant *Escherichia coli*, Moderate | Moderate Methicillin Resistant *Staphylococcus aureus*, light *Corynebactenum* species (consistent with skin flora) |
| Moderate *Staphylococcus aureus* | Moderate *Staphylococcus aureus* |
| Light *Pantoea calida* | Skin flora, light *Corynebacterium jeikeium* |

Results in Table 2 are qualitative. Cultures were obtained by the wound care nurse, with a cotton swab, in the center of the study ulcer.

For the primary endpoint of safety and tolerability, no serious adverse events or withdrawals from the study occurred. One patient in the 1.8% concentration cohort received a pre-planned 50% dose reduction after 2 weeks of topical sodium nitrite treatment because the ulcer size decreased to smaller than half the starting size, and was healed by week 5. Two additional patients in the 1.8% concentration cohort (cohort 3a) were treated at the 1.5% concentration after the first application of the cream, because of asymptomatic decreases in diastolic blood pressure. These patients were assessed for toxicity in the 1.8% cohort and for efficacy in the 1.5% cohort.

No treatment-related or other deaths occurred during the study, and no patient discontinued the trial because of drug-related toxicities. Grade 1 adverse events were reported by 12 (67%) of the 18 patients; Table 3 lists those events that were possibly or probably related to topical sodium nitrite. The most frequently reported adverse event possibly related to study drug was a grade 1 decrease in diastolic blood pressure below a predetermined threshold of 50 mm Hg. Before study drug application, four patients (one in cohort 3, two in 3a, and one in cohort 4) had transient asymptomatic episodes of diastolic blood pressure falling to lower than 50 mm Hg, which also occurred after study drug application in three of these patients and in four additional patients. Attribution to study drug was classified as "possibly related" for the latter four patients (one in cohort 2, two in cohort 3a, and one in cohort 4) (Table 3). None of the patients had a clinically significant decrease in systolic blood pressure or mean arterial pressure, nor needed any intervention to increase their blood pressure. All events were asymptomatic, resolved spontaneously within 1 hour (i.e., at the next blood pressure check), and were judged to be not clinically significant.

TABLE 3

Adverse events probably or possibly related to study cream, by dose cohort

| | Patients (n) | Cohort (sodium nitrite concentration, %) | Outcome Grade |
| --- | --- | --- | --- |
| Pruritus | 2 | 1 (0.5%), 4 (2.0%) | Resolved 1 |
| Burning | 3 | 3 (1.5%), 3a (1.8%), and 4 (2.0%) | Resolved 1 |
| Hypoxia (91%) | 1 | 3 (1.5%) | Resolved 1 |
| Diastolic blood pressure <50 mmHg after application only | 4 | One patient in cohort 2 (1.0%), two in 3a (1.8%), and one in cohort 4 (2.0%) | Resolved 1 |

Hypotension describes episodes of decreases in diastolic blood pressure below a predefined threshold of 50 mm Hg. Mean arterial blood pressure and systolic blood pressure did not change significantly before and after application of the study drug. One patient in cohort 4 had a significant change in diastolic blood pressure (diastolic blood pressure mean of 58 mm Hg fell to a mean of 51 mm Hg after 24 h). Table 4 provides additional details.

TABLE 4

Laboratory values in the 18 subjects at baseline and at the end of study. Values that were statistically significantly lower at the end of study are in bold.

| Laboratory Variable | Baseline | End of study | p-Value |
|---|---|---|---|
| Methemoglobin (%) | 1.4 ± 0.4 | 1.5 ± 0.3 | 0.82 |
| White Blood Cell (K/uL) | 9.9 ± 4.5 | 8.7 ± 3.1 | 0.01 |
| Hemoglobin (g/dL) | 8.1 ± 1 | 8 ± 0.9 | 0.46 |
| Hematocrit (%) | 23.4 ± 3.2 | 22.9 ± 3 | 0.36 |
| Mean corpuscular volume (fL) | 93.8 ± 17.1 | 95.1 ± 17 | 0.21 |
| Platelet count (K/uL) | 332.3 ± 132.7 | 330.1 ± 147.7 | 0.88 |
| Absolute neutrophil (K/uL) | 5.1 ± 3.2 | 4.3 ± 2.1 | 0.06 |
| Reticulocyte (%) | 8.9 ± 5.8 | 11 ± 5.9 | 0.15 |
| Absolute reticulocyte count (K/uL) | 232.1 ± 180.6 | 302.1 ± 200.1 | 0.25 |
| Sodium (mmol/L) | 139.5 ± 2.1 | 139.3 ± 2.3 | 0.68 |
| Potassium (mmol/L) | 4.5 ± 0.5 | 4.5 ± 0.3 | 0.59 |
| Chloride (mmol/L) | 105.8 ± 2.7 | 106.1 ± 2.6 | 0.70 |
| Total $CO_2$ (mmol/L) | 25.3 ± 2.8 | 24.5 ± 2.7 | 0.14 |
| Creatinine (mg/dL) | 0.7 ± 0.2 | 0.7 ± 0.2 | 0.73 |
| Glucose (mg/dL) | 93.5 ± 15.1 | 87.1 ± 12.3 | 0.07 |
| Blood urea nitrogen (BUN) (mg/dL) | 11.7 ± 6.6 | 10.2 ± 5.9 | 0.05 |
| Albumin (g/dL) | 4 ± 0.4 | 4 ± 0.2 | 0.75 |
| Calcium (mmol/L) | 2.2 ± 0.1 | 2.2 ± 0.1 | 0.21 |
| Magnesium (mmol/L) | 0.8 ± 0.1 | 0.8 ± 0.1 | 0.72 |
| Phosphorus (mg/dL) | 3.8 ± 0.4 | 3.9 ± 0.4 | 0.43 |
| Alkaline phosphatase (U/L) | 103.7 ± 38.8 | 100.6 ± 39.4 | 0.78 |
| Alanine aminotransferase (U/L) | 34.2 ± 18.2 | 29.7 ± 17 | 0.07 |
| Aspartate aminotransferase (U/L) | 46.6 ± 23.4 | 44 ± 22.4 | 0.39 |
| Total bilirubin (mg/dL) | 2.5 ± 1.5 | 2.7 ± 1.7 | 0.59 |
| Direct bilirubin (mg/dL) | 0.5 ± 0.2 | 0.5 ± 0.2 | 0.82 |
| Lactate dehydrogenase (U/L) | 509.2 ± 247.3 | 507.6 ± 242.2 | 0.87 |
| Total protein (g/dL) | 8 ± 0.5 | 7.8 ± 0.5 | 0.03 |
| Creatine kinase (U/L) | 91.4 ± 89 | 72.4 ± 58.4 | 0.18 |
| Uric acid (mg/dL) | 7.9 ± 8.6 | 6 ± 1.8 | 0.63 |

An examination of all blood pressures 24 h before and after first application showed no statistically significant changes in diastolic blood pressure by cohort. No association between plasma levels of nitrite and nitrate and changes in blood pressure were recorded.

Figure 7A:
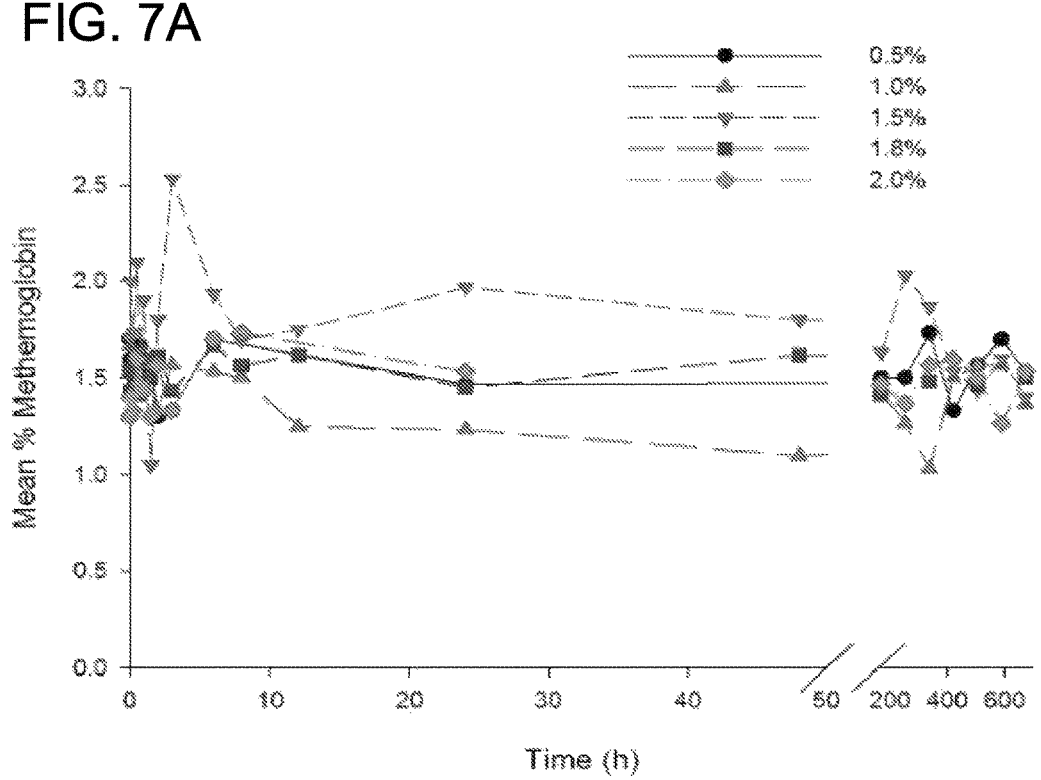
FIG. 7A-7D is a series of graphs illustrating pharmacokinetic analyses during treatment of leg ulcers with topical sodium nitrite.
Figure 7B:
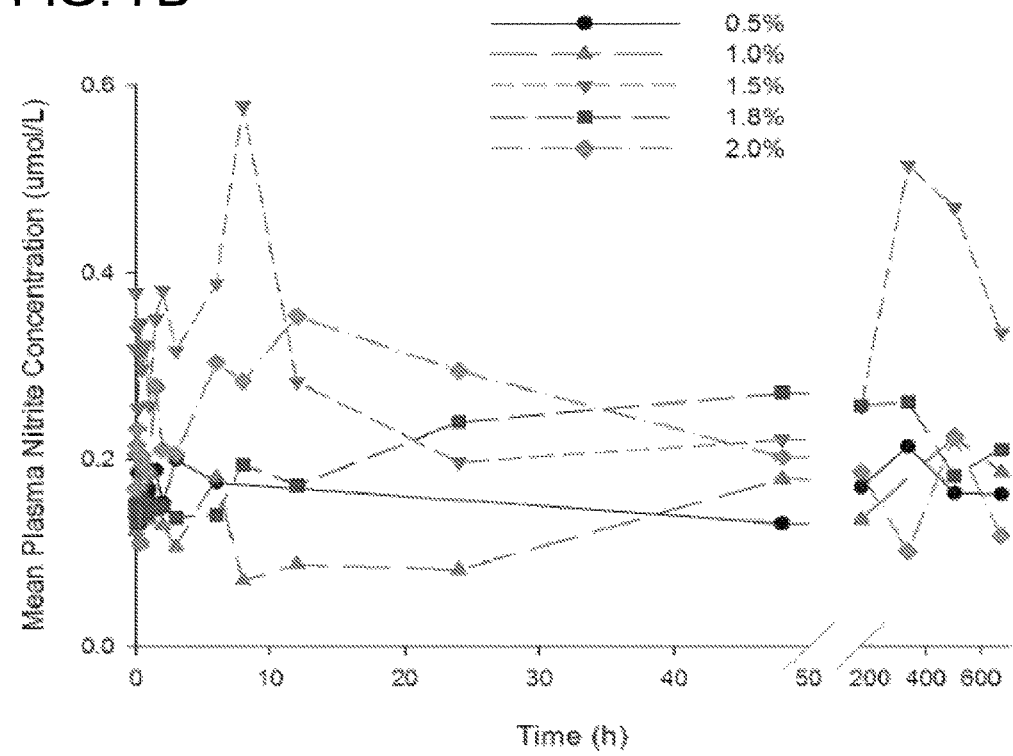
Figure 7C:
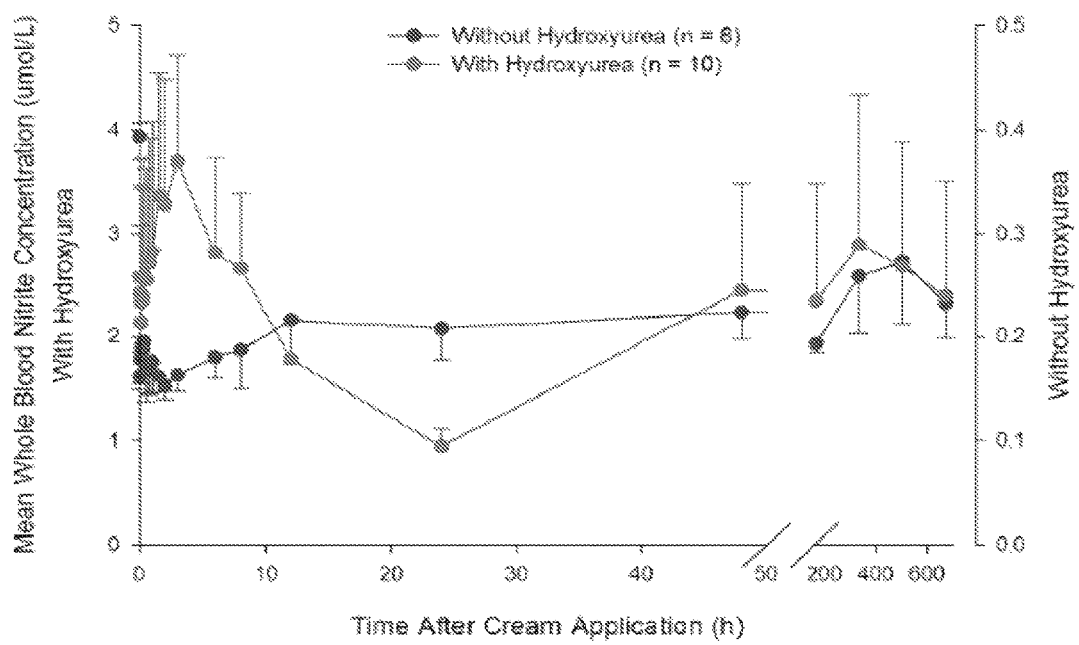
Figure 7D:
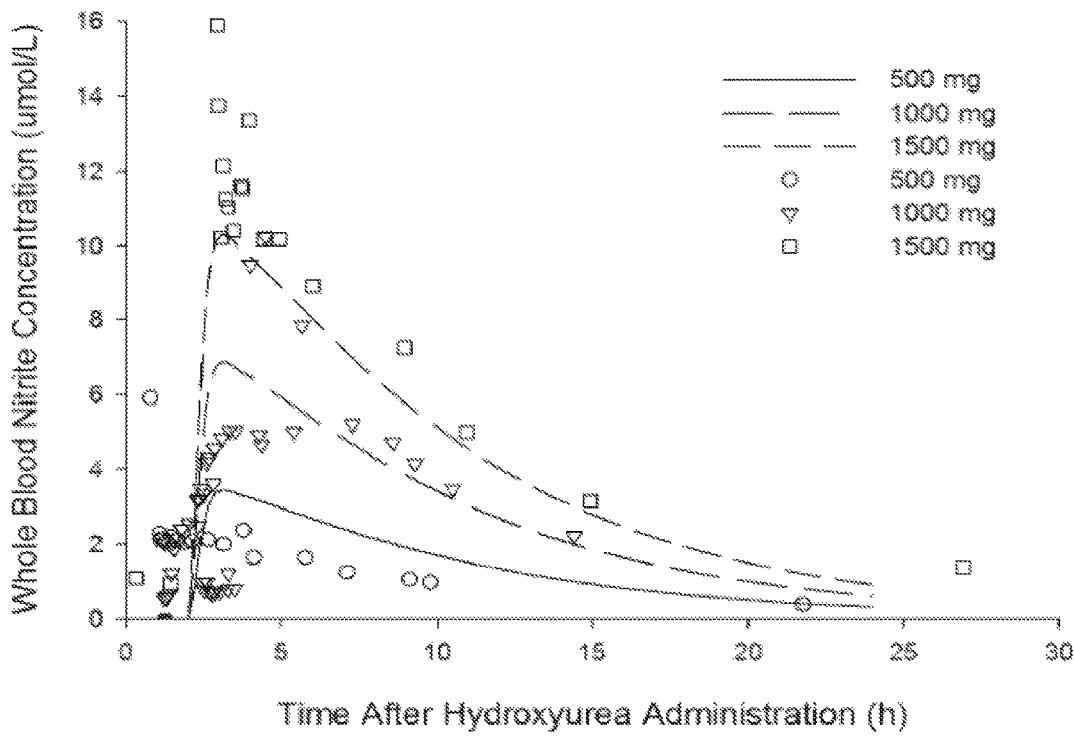

No clinically significant changes in laboratory parameters occurred during the study (Table 4). Statistically significant decreases in mean white blood cell count, from $9.9 \times 10^9$/L (SD 4.5) to $8.7 \times 10^9$/L (SD 3.1) (p=0.0102), and mean total protein, from 80 g/L (SD 0.5) to 78 g/L (SD 0.5) (p=0.0302), were recorded. Methemoglobin did not change significantly (p=0.82)—it peaked at 4.1% in one patient in cohort 3 (the 1.5% concentration cohort) 90 min post-application, and decreased spontaneously (FIG. 7A). Assessment of plasma nitrite, nitrate, and whole blood nitrite concentrations in the first 48 h showed that only patients receiving hydroxycarbamide had consistent whole blood nitrite concentration-time profiles (FIG. 7A-7D). Therefore, we did a subsequent pharmacokinetic analysis was carried out with respect to the time and dose of hydroxycarbamide intake instead of nitrite cream administration, using a population approach. A two-compartment model was fitted with first-order absorption and elimination to whole blood nitrite concentrations using first-order conditional estimation method by Phoenix NLME 1.2 (Certara USA Inc., St Louis, Mo., USA), and an exponential model was used to describe the inter-individual variability and a mixed-ratio model to describe the intra-individual variability (FIG. 7C). No such profile was recorded in the eight patients who were not receiving hydroxycarbamide (FIG. 7C).

Figure 1B:
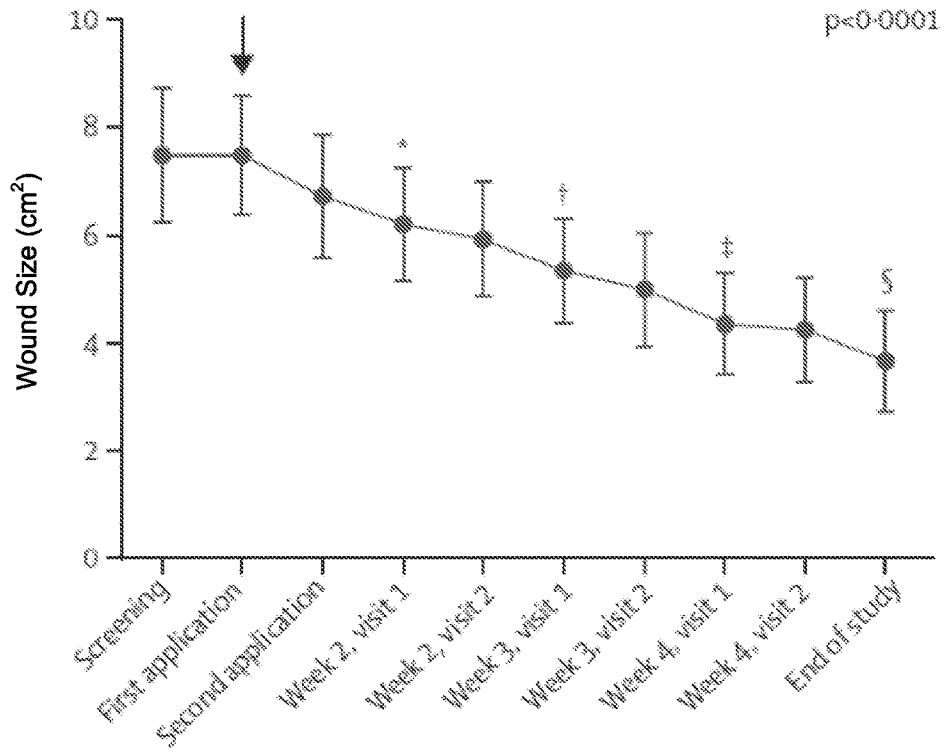
Figure 1C:
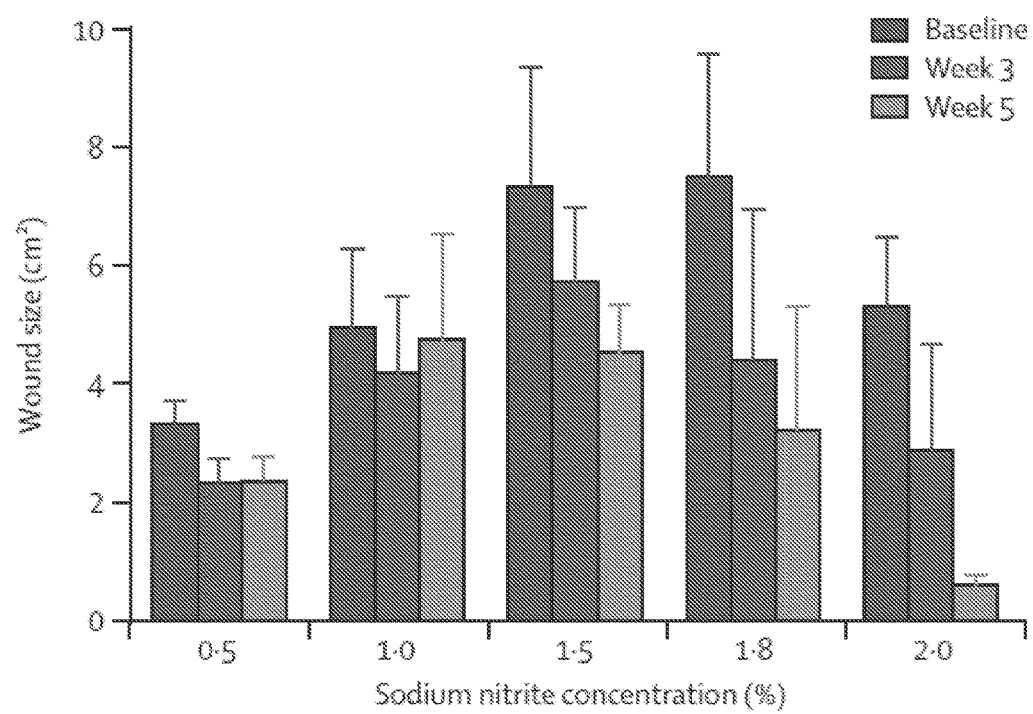

Significant reductions in ulcer size and pain were recorded during treatment with topical sodium nitrite, generally with signs of dose dependence. Mean ulcer surface area at study entry was 5.97 $cm^2$ (SD 3.40; range 2.51-14.66 $cm^2$) measured by digital photography and 7.50 $cm^2$ (SD 4.65; range 2.09-16.50 $cm^2$) according to manual measurements, and decreased to 3.26 $cm^2$ (SD 2.72; range 0-9.39 $cm^2$, p=0.0003) on digital photography, and 3.67 $cm^2$ (SD 3.97; range 0-14.07 $cm^2$, p<0.0001) with manual measurements after treatment (FIG. 1A, 1B). 17 (94%) of 18 ulcers decreased in size by the end of the study, and 13 (72%) of 18 of ulcers had a greater than 25% decrease in surface area by digital photography (14 [78%] of 18 had this decrease according to manual measurements). From baseline to the end of the study, the study ulcer size decreased by a mean of 29.9% for cohort 1 (0.5% sodium nitrite), 7.7% for cohort 2 (1% sodium nitrite; one patient in this cohort progressed), 32.5% for cohort 3 (1.5% sodium nitrite), 69.7% for cohort 3a (1.8% sodium nitrite; one complete closure), and 88.3% for cohort 4 (2% sodium nitrite, two complete closures; Table 5). These reductions in wound size correlated with nitrite dose cohort (Spearman's correlation coefficient 0.7, p=0.0012; FIG. 1C). Hydroxycarbamide use and fetal haemoglobin level were not associated with ulcer healing (p=0.96 and p=0.38, respectively). Chronic transfusion therapy (in three of 18 patients) had a weak association with percent closure (i.e., percentage reduction in wound surface area from baseline to the end of the study) at the end of the trial (p=0.0126).

TABLE 5

Percentage reduction in ulcer surface area from baseline in each cohort

| | Sodium nitrite concentration | Patients (n) | Reduction at week 3 | Reduction at end of study |
|---|---|---|---|---|
| Cohort 1 | 0.5% | 3 | 31.1% | 29.9% |
| Cohort 2 | 1.0% | 3 | 17.4% | 77% (one ulcer progressed) |
| Cohort 3 | 1.5% | 5 | 17.3% | 32.5% |
| Cohort 3a | 1.8% | 4 | 56.1% | 69.7% (one ulcer healed) |
| Cohort 4 | 2.0% | 3 | 54.9% | 88.3% (two ulcers healed) |

Measurements of ulcer surface area were done by digital planimetry. Reduction in wound size correlates with nitrite dose cohort (Spearman's correlation coefficient 0.7; p = 0.0012).

Figure 2A:
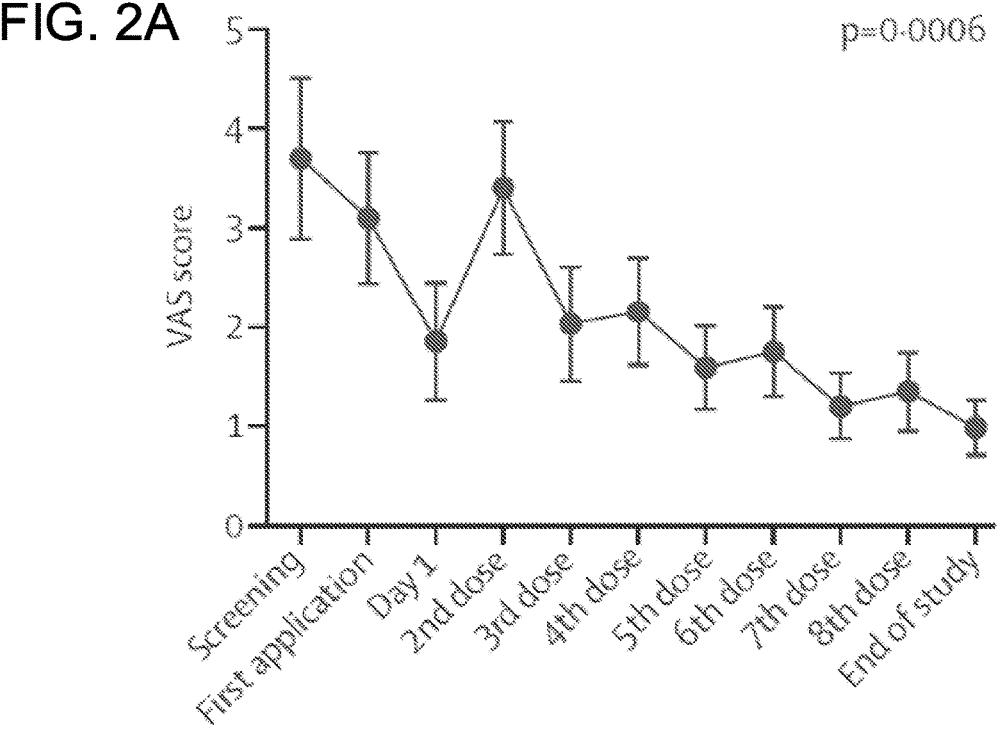
FIG. 2A-2D is a series of graphs illustrating changes in leg ulcer pain during the topical sodium nitrite treatment period. Patients were asked to score pain from the ulcer treated with topical sodium nitrite and any additional ulcers not treated with topical sodium nitrite.
Figure 2B:
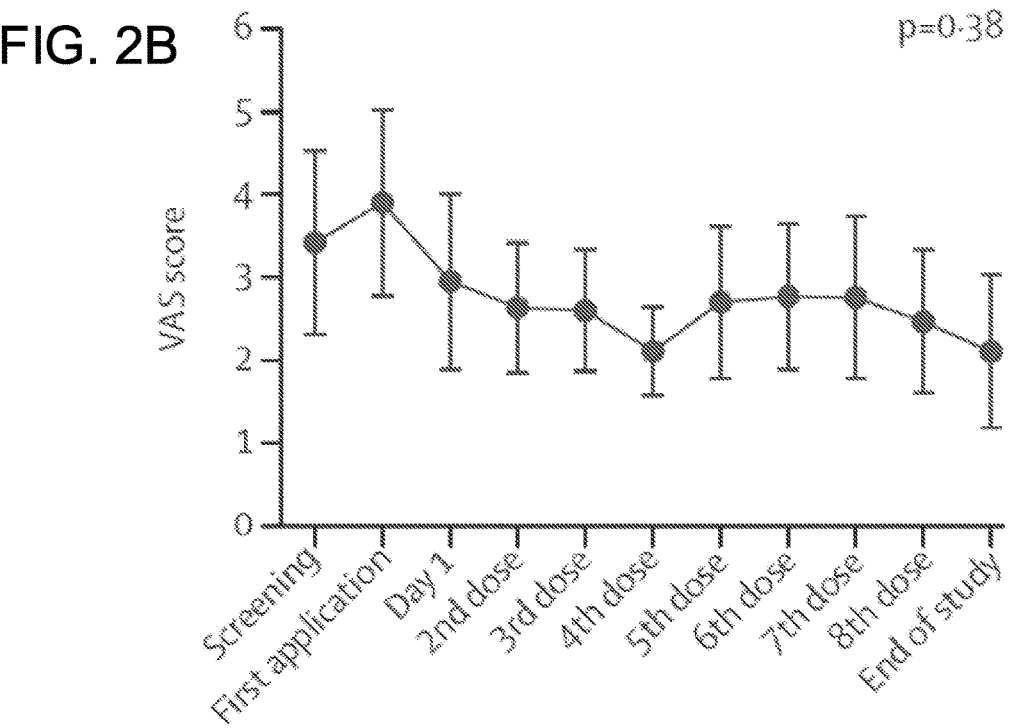
Figure 2C:
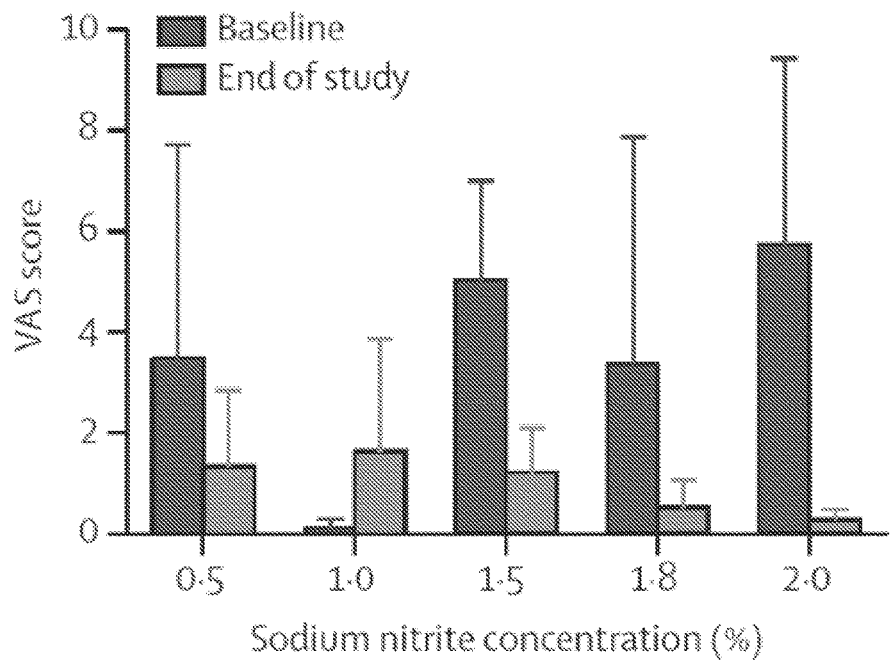
Figure 2D:
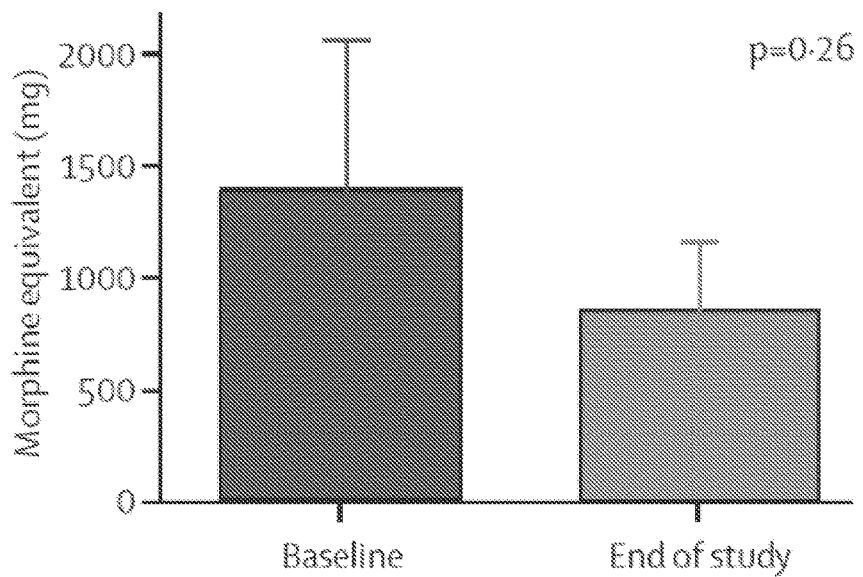

Pain at the study ulcer decreased significantly during the study: the mean visual analogue scale score before application of sodium nitrite was 3.7 cm (SD 3.4; range 0-10) and decreased to 1.0 cm (1.2; 0-4.2) at the end of the study (FIG. 2A) (p=0.0006). FIG. 2C shows the changes in visual analogue scale (VAS) score according to cohort. In the nine patients who had more than one ulcer, visual analogue scale scores for non-treated ulcers did not change significantly during the trial (mean 3.4 cm [SD 3.3; range 0-9.6] at the beginning of the trial, and mean 2.1 cm [2.8; 0-6.4] at the completion of the trial; p=0.38) (FIG. 2B). Opioid analgesic use decreased over time, but this reduction was not significant (1379.2 mg morphine equivalents the week before treatment vs 804.8 mg the week after [p=0.26]; FIG. 2D).

Brief pain inventory scores for severity and interference improved significantly at the end of the study (p=0.0048 for severity and p=0.0013 for interference; FIG. 3A, 3B). Baseline brief pain inventory pain severity and interference scores correlated with C-reactive protein level at baseline (with severity score: Spearman's correlation coefficient 0.55 [p=0.0182], and with interference score: Spearman's correlation coefficient 0.47 [p=0.0488]), but not with ulcer age, initial size, hydroxycarbamide use, transfusions, and percentage of haemoglobin S or haemoglobin F. The changes in pain severity (FIG. 3C), pain interference (FIG. 3D), and visual analogue scale scores did not correlate with sodium nitrite cohort, nor did they correlate with ulcer size reduction.

Figure 4A:
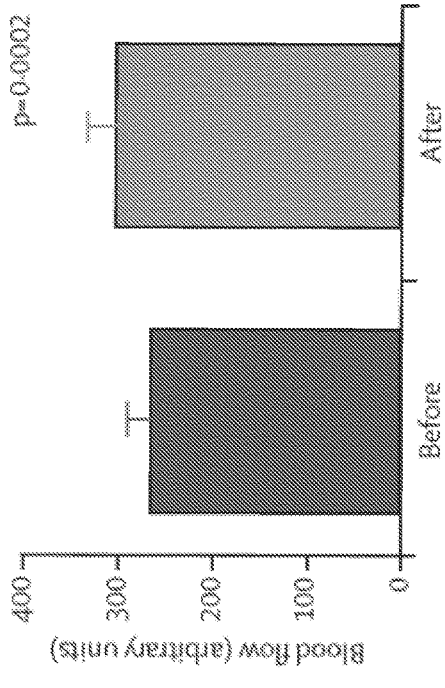
FIG. 4A-4D is a series of graphs quantifying cutaneous imaging before and after first application of topical sodium nitrite cream. Changes after the first application of sodium nitrite cream for all 18 trial participants in cutaneous periwound temperature by infrared thermography (FIG. 4A) and cutaneous periwound blood flow by laser speckle contrast imaging (FIG. 4B). The infrared thermography and laser speckle contrast measurement of cutaneous blood flow data are calculated by spatial averaging of the region of interest followed by time averaging over the 5 min before application of sodium nitrite cream and the final 5 min of the imaging 30 min after the application.
Figure 4B:
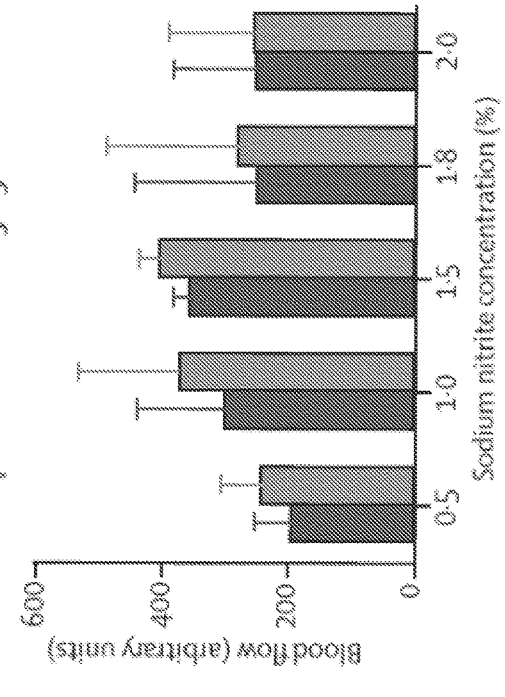
Figure 4C:
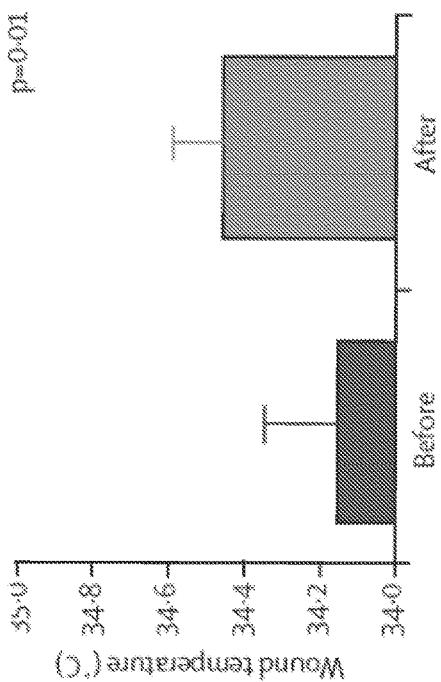
Figure 4D:
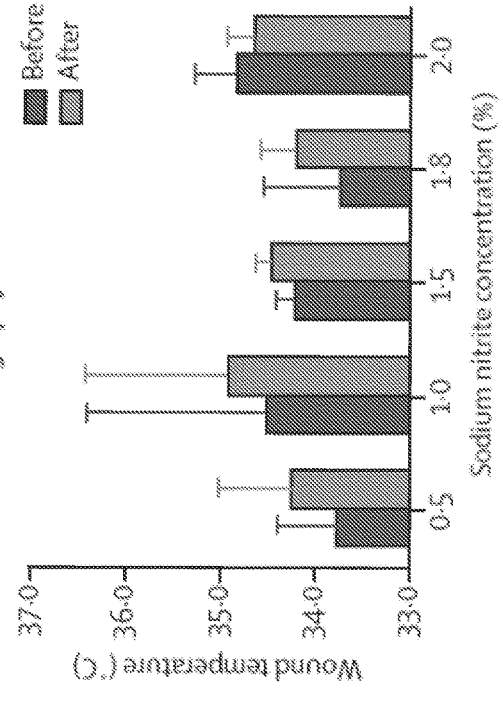
Figure 6A:
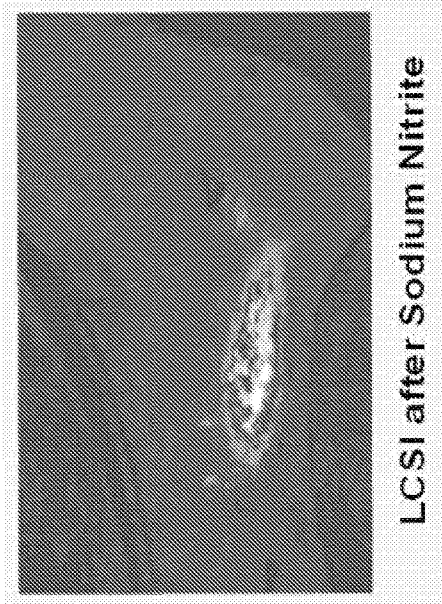
FIG. 6A-6D is a series of images, illustrating laser speckle contract imaging (LSCI) (FIG. 6A-6B) and infrared (FIG. 6C-6D) images of a leg ulcer in a representative sickle cell disease patient before (FIG. 6A-6C) and after (FIG. 6B-6D) treatment with sodium nitrite.
Figure 6B:
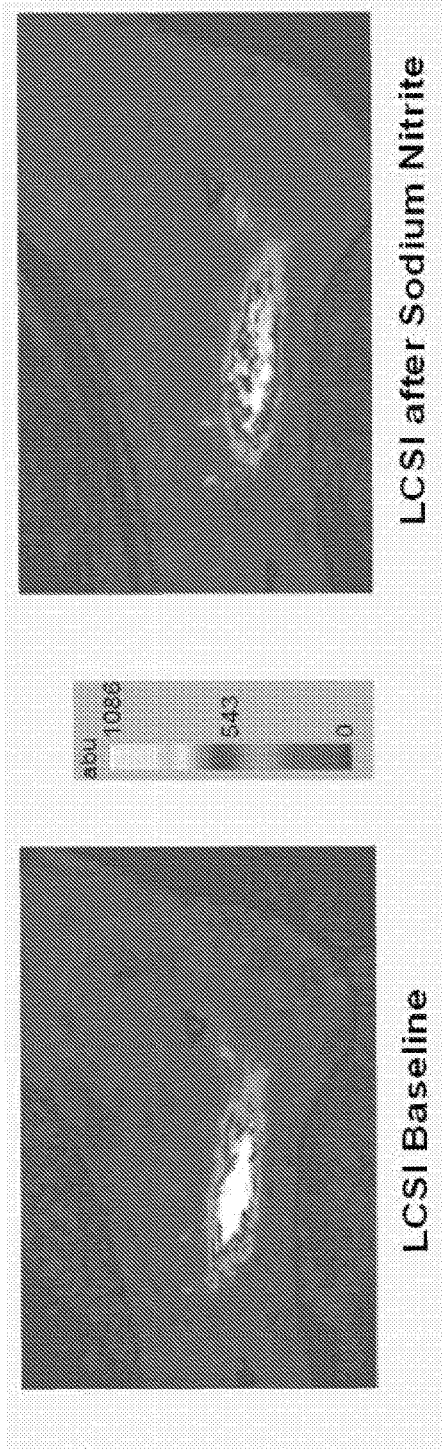
Figure 6D:
Figure 6C:
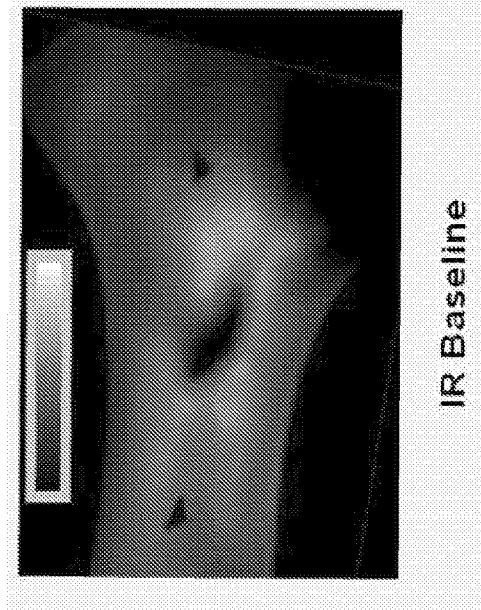

Laser speckle contrast imaging showed a significant increase in regional blood flow after the first cream application (from 272.0 [SD 137.3] to 312.1 [150.6], p=0.0002) (FIG. 4B), and a smaller, non-significant increase after the second application (237.5 [SD 117.5] to 262.8 [137.4], p=0.10). This treatment effect of increased cutaneous periwound blood flow by laser speckle contrast imaging was corroborated by increased periwound skin temperature measured by infrared thermography (FIG. 4A) after the first dose (mean 34.2° C. [SD 0.9] to 34.5° C. [SD 0.7], p=0.0119) and after the second dose (34.1° C. [SD 0.8] to 34.5° C. [SD 0.8], p=0.0008; data not shown). The mean temperature in the wound bed itself increased significantly, from 32.8° C. (SD 1.4) to 34.9° C. (0.7) after the first cream application (p<0.0001), and from 33.0° C. (SD 1.1) to 34.8° C. (0.7) after the second (p<0.0001) and increased in parallel in the periwound region (Spearman's correlation coefficient 0.72, p=0.0010). The increase in skin periwound temperature and regional blood flow did not correlate with sodium nitrite dose cohort (FIG. 4C, 4D).

FIG. 5A-5F shows visible spectrum (FIG. 5A-5C) and infrared (FIG. 5D-5F) images of a leg ulcer in a representative sickle cell disease patient throughout the treatment period, as indicated. FIG. 6A-6D show laser speckle contract imaging (LSCI) (FIG. 6A, 6B) and infrared (FIG. 6C, 6D) images of a leg ulcer in a representative sickle cell disease patient before (FIG. 6A-6C) and after (FIG. 6B-6D) treatment with sodium nitrite.

Discussion

Findings from this small phase 1-2 safety and tolerability dose-finding study show that sodium nitrite, e.g., 2% cream, is well tolerated, with preliminary indications of efficacy. Evidence of efficacy is not usually expected from an early phase trial. Surprisingly, however, several of the prospectively specified secondary outcome efficacy variables showed statistical significance.

Pharmacokinetic analysis showed that topical sodium nitrite was minimally absorbed, which is consistent with the absence of systemic effects. Whole blood nitrite concentrations increased after ingestion of hydroxycarbamide and not after sodium nitrite application, which confirms previous reports of hydroxycarbamide as a donor of nitric oxide that is converted to nitrite (King, Curr Top Med Chem.; 5: 665-673, 2005; Cokic et al., Blood.; 108: 184-191, 2006). The possibility of clinically significant systemic absorption was anticipated as a possible issue, but in reality this turned out to be negligible and clinically insignificant. Asymptomatic events of diastolic blood pressure below a predetermined limit of 50 mm Hg were detected in some patients both before and after topical sodium nitrite application, with no association with plasma levels of nitrite and nitrate, all of which suggest that blood pressure changes are not a side effect of the tested concentrations of topical sodium nitrite. Although the statistical power of this study is too low to detect small changes in blood pressure related to plasma levels of nitrite or nitrate, clinically significant systemic blood pressure changes are not expected with these poorly absorbed topical doses of sodium nitrite that, even if fully absorbed, would provide only half of the dose amounts reported to cause systemic effects when administered intravenously (Mack et al., Br J Haematol.; 142: 971-978, 2008; Oplander et al., Nitric Oxide.; 26: 132-140, 2012).

Patients with sickle cell disease have lower blood pressure than do healthy African-American controls (Pegelow et al., Am J Med.; 102: 171-177, 1997), and patients with sickle cell disease and leg ulcers have an even lower diastolic blood pressure than do those without leg ulcers (Minniti et al., Am J Hematol.; 86: 705-708, 2011). In a post-hoc analysis to establish the frequency of diastolic blood pressure lower than 50 mm Hg in an existing database of blood pressure measurements from adults with sickle cell disease at the same clinical site, for the purposes of comparison, diastolic blood pressures were not significantly lower in 18 patients with sickle cell disease and leg ulcers treated with sodium nitrite than in 15 adults with sickle cell disease and leg ulcers followed in a separate NIH natural history protocol (ClinicalTrials.gov identifier NCT00081523) using standard of care treatments. In fact, during 12 days of blood pressure monitoring for the two sets of patients, only 30 (7%) of the 403 diastolic blood pressure measurements in the nitrite group fell below 50 mm Hg, compared with 11 (13%) of the 82 blood pressure measurements in the sickle cell disease natural history group (p=0.005). Occurrences of low diastolic blood pressure seem to be a previously unappreciated characteristic of adults with sickle cell disease and leg ulcers, which might warrant additional investigation, but do not seem to be induced by topical sodium nitrite.

The above results suggest that topical sodium nitrite has a dose-dependent effect on wound healing. A rapid decrease in wound size was recorded, with complete closure of three ulcers treated with the highest concentrations of sodium nitrite cream, and a mean reduction in ulcer size that ranged from 30% at the lowest concentration to 88% with the highest. This apparent dose-response association between topical sodium nitrite concentration and the rate of healing helps to mitigate the acknowledged potential confounding effects of bed rest during the patients' 4.5-day stay in hospital and consistent wound care in promoting wound healing during the protocol. This preliminary indication of therapeutic effect is further supported by the decrease in pain rating only at the ulcers treated with topical sodium nitrite and not at ulcers treated only with standard of care, although this subjective finding is subject to placebo effect.

The apparently increased rate of wound healing in this initial open-label dose-finding study is encouraging because these 18 patients had chronic wounds that were established for 10-300 months before the study, and wounds in patients with sickle cell anaemia have previously been reported to often heal very slowly, over periods of months to years (Serjeant, et al., Hematol Oncol Clin North Am.; 19: 943-956 (viii-ix.), 2005). Improvement in wound size after 4 weeks has been shown to be predictive of eventual healing in chronic wounds in the general population (Phillips et al., J Am Acad Dermatol.; 43: 627-630, 2000).

The decrease in ulcer pain in this trial is intriguing. Pain at the ulcer site is a characteristic of sickle cell disease ulcers, which differentiates them from typical venous ulcers and contributes substantially to the morbidity of sickle cell leg ulcers (Halabi-Tawil et al., Br J Dermatol.; 158: 339-344, 2008), affecting patients' quality of life, ability to work, mood, and sleep pattern (Upton & Andrews, J Wound Care.; 22: 389-390 (392, 394), 2013; Hareendran et al., J Wound Care.; 14: 53-57, 2005). Affected patients often need chronic systemic opioid analgesics for pain, as was the case in the subject patient population. The improvement in pain might be related to improved regional blood flow and reduced ischaemia, or to decreased inflammation caused by the known bacteriostatic effects of nitrite, or both these effects. Of great interest is the finding that the decrease in pain was not related to the reduction in ulcer size, but occurred independently of it, even in patients who did not experience notable healing. These results add to existing data from animals and human beings that suggest a role for nitric oxide and nitric oxide synthase in pain signalling. In future topical sodium nitrite trials, it will be worthwhile to examine whether the observed nonsignificant reduction in opioid analgesia use might be significant in a larger trial with greater statistical power.

The increases in both laser speckle contrast imaging and periwound and wound skin temperature after application of sodium nitrite cream provide evidence of a quantitative physiological response and serve as proof of principle that topical nitrite penetrates the wound and modifies local vascular physiology within minutes of its application. Nitrite acidified by ascorbic acid has been used as a nitric oxide generator system, probably providing bursts of nitric oxide over short periods by a disproportionation reaction that can cause tissue and cell death, DNA damage, and changed mitochondrial function (Shiva & Gladwin, *Basic Res Cardiol.;* 104: 113-119, 2009; Kroncke et al., *Nitric Oxide.;* 1: 107-120, 1997; Bolanos et al., *J Neurochem.;* 68: 2227-2240, 1997). The herein-reported results support a hypothesis that acidification of nitrite is not needed to promote wound healing. The non-acidified preparation used in this study is stable, and hypothetically acts as a nitric oxide prodrug specifically after slow absorption into ischaemic wounds.

The established property of nitrite to deliver nitric oxide targeted to ischaemic tissue provides an attractive rationale for its mechanism of action in sickle cell leg ulcers. The increase in regional blood flow recorded after cream application supports the hypothesis that nitric oxide functions as a local vasodilator and causes beneficial improvements in microcirculation. The physiological and clinical responses to topical sodium nitrite reported in this open-label dose-finding trial, coupled with its apparent safety and tolerability, provide encouragement to develop placebo-controlled phase 2 trials in patients with sickle cell disease who have non-healing leg ulcers.

In the general US population, the cost for medical care of chronic wounds is estimated to be more than US$25 billion (Sen et al., *Wound Repair Regen.;* 17: 763-771, 2009). Therefore, it is thought-provoking to consider the potential effect of extending future trials of topical sodium nitrite for chronic wounds in these other populations, such as patients with diabetes, who share similar problems with those affected by sickle cell anaemia including low nitric oxide bioavailability, vasculopathy, poor cutaneous blood flow, and skin ulceration with slow healing.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A non-acidified formulation for topical administration, comprising an aqueous solution of about 0.5% to about 3.0% by weight non-acidified sodium nitrite dispersed in a white petrolatum ointment, wherein the white petrolatum ointment comprises white petrolatum, mineral oil, ceresin, panthenol and bisabolol.

2. The formulation of claim 1, wherein the white petrolatum ointment comprises a 41% petrolatum ointment.

3. The formulation of claim 1, wherein the concentration of sodium nitrite is 0.5, 1.0, 1.5, 1.8, 2.0, 2.5 or 3.0% by weight.

4. A method of preparing the formulation of claim 1, comprising:
dissolving sodium nitrite powder in water to produce an aqueous solution of sodium nitrite having a concentration of about 20% to about 40% sodium nitrite;
filtering the aqueous solution of sodium nitrite through a 0.22 micron filter; and
dispersing the filtered aqueous solution of nitrite into the white petrolatum ointment.

5. The method of claim 4, wherein the concentration of the aqueous solution of sodium nitrite is about 30% sodium nitrite.

6. The method of claim 4, wherein the volume of the aqueous solution dispersed into the white petrolatum ointment is about 4% to about 5% v/w.

7. The formulation of claim 1, wherein the formulation has a pH of about 6.0-8.5.

8. A formulation for topical administration, comprising an aqueous solution of about 0.5% to about 3.0% by weight non-acidified sodium nitrite dispersed in a white petrolatum ointment, wherein the white petrolatum ointment comprises white petrolatum, mineral oil, ceresin, panthenol and bisabolol, and wherein the formulation does not comprise an acid or an acidifying agent.

9. A formulation for topical administration, consisting of an aqueous solution of about 0.5% to about 3.0% by weight non-acidified sodium nitrite dispersed in a white petrolatum ointment.

* * * * *